(12) United States Patent
Uematsu et al.

(10) Patent No.: US 10,241,033 B2
(45) Date of Patent: *Mar. 26, 2019

(54) SPECTROSCOPIC SENSOR DEVICE AND ELECTRONIC EQUIPMENT

(71) Applicant: SEIKO EPSON CORPORATION, Tokyo (JP)

(72) Inventors: Akira Uematsu, Suwa (JP); Yoichi Sato, Suwa-gun (JP); Akira Komatsu, Kamiina-gun (JP); Kunihiko Yano, Shiogiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 71 days.

This patent is subject to a terminal disclaimer.

(21) Appl. No.: 15/190,875

(22) Filed: Jun. 23, 2016

(65) Prior Publication Data

US 2016/0305868 A1 Oct. 20, 2016

Related U.S. Application Data

(60) Division of application No. 14/341,221, filed on Jul. 25, 2014, now Pat. No. 9,400,213, which is a (Continued)

(30) Foreign Application Priority Data

Mar. 5, 2010 (JP) .................................. 2010-048848

(51) Int. Cl.
*G01N 21/25* (2006.01)
*G01N 21/31* (2006.01)
(Continued)

(52) U.S. Cl.
CPC ................ *G01N 21/31* (2013.01); *G01J 3/02* (2013.01); *G01J 3/0256* (2013.01);
(Continued)

(58) Field of Classification Search
None
See application file for complete search history.

(56) References Cited

U.S. PATENT DOCUMENTS 4,222,667 A 9/1980 Layne
4,810,870 A 3/1989 Tsuno et al.
(Continued)

FOREIGN PATENT DOCUMENTS

DE 102006039073 A1 2/2008
EP 1 528 380 A1 5/2005
(Continued)

OTHER PUBLICATIONS

Jan. 4, 2016 Office Action issued in U.S. Appl. No. 14/341,221.
(Continued)

*Primary Examiner* — Tri Ton
*Assistant Examiner* — Rufus Phillips
(74) *Attorney, Agent, or Firm* — Oliff PLC

(57) ABSTRACT

A spectroscopic sensor that applies lights in a wavelength band containing plural wavelengths to an object and spectroscopically separates reflected lights or transmitted lights from the object using plural light band-pass filters that transmit the respective specific wavelengths and plural photosensor parts to which corresponding transmitted lights are input based on output results of independent photosensors. The spectroscopic sensor may be integrated in a semiconductor device or module by integration using a semiconductor process and downsizing may be realized.

18 Claims, 18 Drawing Sheets

Related U.S. Application Data continuation of application No. 13/038,799, filed on Mar. 2, 2011, now Pat. No. 8,848,187.

(51) Int. Cl.

| | | |
|---|---|---|
| *G01J 3/02* | (2006.01) | |
| *G01J 3/36* | (2006.01) | |
| *G02B 5/28* | (2006.01) | |
| *G02B 7/00* | (2006.01) | |
| *H01L 27/144* | (2006.01) | |
| *H01L 27/146* | (2006.01) | |
| *G01J 3/28* | (2006.01) | |
| *G01J 3/51* | (2006.01) | |
| *G01J 3/12* | (2006.01) | |

(52) U.S. Cl.
CPC ........... *G01J 3/0259* (2013.01); *G01J 3/0262* (2013.01); *G01J 3/0278* (2013.01); *G01J 3/28* (2013.01); *G01J 3/36* (2013.01); *G01J 3/51* (2013.01); *G02B 5/285* (2013.01); *G02B 7/006* (2013.01); *H01L 27/1443* (2013.01); *H01L 27/14625* (2013.01); *G01J 2003/1226* (2013.01)

(56) References Cited

U.S. PATENT DOCUMENTS

| | | | |
|---|---|---|---|
| 4,894,700 A * | 1/1990 | Nobue | H01L 27/14621 257/435 |
| 5,131,391 A | 7/1992 | Sakai et al. | |
| 5,144,498 A | 9/1992 | Vincent | |
| 5,170,786 A | 12/1992 | Thomas et al. | |
| 5,564,417 A | 10/1996 | Chance | |
| 5,594,236 A | 1/1997 | Suzuki et al. | |
| 5,615,673 A | 4/1997 | Berger et al. | |
| 5,779,631 A | 7/1998 | Chance | |
| 5,873,821 A | 2/1999 | Chance et al. | |
| 5,879,294 A | 3/1999 | Anderson et al. | |
| 6,134,460 A | 10/2000 | Chance | |
| 6,211,916 B1 | 4/2001 | Hawkins et al. | |
| 6,246,892 B1 | 6/2001 | Chance | |
| 6,263,221 B1 | 7/2001 | Chance et al. | |
| 6,344,666 B1 | 2/2002 | Yamaguchi et al. | |
| 6,397,099 B1 | 5/2002 | Chance | |
| 6,521,882 B1 | 2/2003 | Sumiya et al. | |
| 6,549,795 B1 | 4/2003 | Chance | |
| 6,590,660 B2 | 7/2003 | Jung et al. | |
| 6,639,669 B2 | 10/2003 | Hubble, III et al. | |
| 6,653,617 B2 | 11/2003 | Hiyama et al. | |
| 6,708,048 B1 | 3/2004 | Chance | |
| 7,315,378 B2 | 1/2008 | Phelan et al. | |
| 7,345,330 B2 | 3/2008 | Rhodes | |
| 7,355,714 B2 | 4/2008 | Wang et al. | |
| 7,416,915 B2 | 8/2008 | Kasano et al. | |
| 7,623,166 B2 | 11/2009 | Inaba et al. | |
| 2002/0161290 A1 | 10/2002 | Chance | |
| 2002/0183624 A1 | 12/2002 | Rowe et al. | |
| 2003/0023140 A1 | 1/2003 | Chance | |
| 2003/0078504 A1 | 4/2003 | Rowe | |
| 2004/0065910 A1 | 4/2004 | Yoshiaki et al. | |
| 2005/0035304 A1 | 2/2005 | Colvin et al. | |
| 2005/0113656 A1 | 5/2005 | Chance | |
| 2005/0173773 A1 * | 8/2005 | Kim | H01L 27/14601 257/431 |
| 2006/0186547 A1 | 8/2006 | Wang et al. | |
| 2006/0285005 A1 | 12/2006 | Inaba et al. | |
| 2007/0139765 A1 | 6/2007 | Daniel et al. | |
| 2007/0210344 A1 * | 9/2007 | Arao | H01L 27/14623 257/232 |
| 2007/0290284 A1 | 12/2007 | Shaffer | |
| 2008/0068592 A1 * | 3/2008 | Uchida | A61B 5/0059 356/73 |
| 2008/0124915 A1 * | 5/2008 | Yamaguchi | H01L 21/76843 438/637 |
| 2008/0297788 A1 | 12/2008 | Rowe et al. | |
| 2008/0304712 A1 | 12/2008 | Rowe et al. | |
| 2009/0189237 A1 * | 7/2009 | Hirano | H01L 27/14625 257/432 |
| 2009/0244711 A1 | 10/2009 | Yokoyama et al. | |
| 2011/0043823 A1 | 2/2011 | Hillmer et al. | |
| 2011/0183460 A1 | 7/2011 | Wang et al. | |
| 2011/0216315 A1 | 9/2011 | Uematsu et al. | |
| 2011/0242526 A1 | 10/2011 | Van Bommel et al. | |
| 2012/0232354 A1 | 9/2012 | Ecker et al. | |
| 2013/0021596 A1 | 1/2013 | Rowe et al. | |
| 2013/0027685 A1 | 1/2013 | Rowe et al. | |
| 2014/0151575 A1 | 6/2014 | Hillmer et al. | |

FOREIGN PATENT DOCUMENTS

| | | |
|---|---|---|
| JP | S61-205827 A | 9/1986 |
| JP | S62-139627 A | 6/1987 |
| JP | H01-35325 | 2/1989 |
| JP | H03-23846 A | 1/1991 |
| JP | H06-129908 A | 5/1994 |
| JP | H06-510920 A | 12/1994 |
| JP | 07167710 | 7/1995 |
| JP | H08-094831 A | 4/1996 |
| JP | H08-509880 A | 10/1996 |
| JP | 2000-031510 A | 1/2000 |
| JP | 2000150849 A | 5/2000 |
| JP | 2001237404 A | 8/2001 |
| JP | 2003090907 A | 3/2003 |
| JP | 2003174155 A | 6/2003 |
| JP | 2003-310579 A | 11/2003 |
| JP | 2006-237576 A | 9/2006 |
| JP | 2006-351800 A | 12/2006 |
| JP | 2007-080918 A | 3/2007 |
| JP | 2008-237686 A | 10/2008 |
| JP | 2008-296051 A | 12/2008 |
| JP | 2009-258691 A | 11/2009 |
| JP | 05087537 B2 | 12/2012 |
| WO | 0131304 A1 | 5/2001 |
| WO | 2010-041198 A1 | 4/2010 |

OTHER PUBLICATIONS

European Search Report dated Jan. 6, 2012 issued in European Patent Application No. 11156872.1.
May 23, 2014 Notice of Allowance issued in U.S. Appl. No. 13/038,799.
Feb. 11, 2014 Office Action issued in U.S. Appl. No. 13/038,799.
Oct. 7, 2013 Office Action issued in U.S. Appl. No. 13/038,799.
Apr. 12, 2013 Election of Species Requirement issued in U.S. Appl. No. 13/038,799.

* cited by examiner (OBJECT OF OBSERVATION)

SPECTROSCOPIC SENSOR DEVICE AND ELECTRONIC EQUIPMENT

CROSS REFERENCE

This is a divisional application of application Ser. No. 14/341,221 filed Jul. 25, 2014 which claims priority to Japanese Patent Application No. 2010-048848 filed Mar. 5, 2010 including the specification, drawings and abstract is incorporated herein by reference in its entirety.

BACKGROUND

1. Technical Field

The present invention relates to a spectroscopic sensor device, electronic equipment, etc.

2. Related Art

In medical, agricultural, environmental fields etc., spectroscopic sensors are used for diagnoses and inspections of objects. For example, in medical fields, pulse oximeters that measure oxygen saturation in the blood using light absorption of hemoglobin are used. Further, in the agricultural fields, sugar content meters that measure the sugar contents of fruits using light absorption of sugar.

However, in spectroscopic sensors in related art, there is a problem that downsizing is difficult. For example, in a spectroscopic sensor that acquires a continuous spectrum, it is necessary to provide a prism for generation of the continuous spectrum or the like and secure an optical path length, and the device becomes larger. Accordingly, it is difficult to provide many sensors, constantly provide sensors for an object to be inspected, or the like.

Here, Patent Document 1 (JP-A-6-129908) discloses a technique of limiting a transmission wavelength band of a filter by limiting the incident angle of incident light using an optical fiber. Further, Patent Document 2 (JP-2006-351800) discloses a technique of sensing light in plural wavelength bands using multilayer filters having different thicknesses with respect to each sensor.

SUMMARY

An advantage of some aspects of the invention is to provide a spectroscopic sensor device, electronic equipment, etc. that can be downsized.

One aspect of the invention relates to a spectroscopic sensor device including a light source unit that applies a light in a wavelength band containing plural wavelengths as targets of detection, and a spectroscopic sensor to which a light obtained by application of the light from the light source unit to an object of observation enters, wherein the spectroscopic sensor has plural light band-pass filters having different transmission wavelengths, and plural photosensor parts, the first light band-pass filter of the plural light band-pass filters has a wavelength characteristic of transmitting a first specific wavelength, the second light band-pass filter of the plural light band-pass filters has a wavelength characteristic of transmitting a second specific wavelength different from the first specific wavelength, the first photosensor of the plural photosensors senses a light having the first specific wavelength transmitted through the first light band-pass filter, and the second photosensor of the plural photosensors senses a light having the second specific wavelength transmitted through the second light band-pass filter.

According to the one aspect of the invention, the light obtained by application of the light from the light source unit to the object of observation is allowed to enter the spectroscopic sensor. Further, the light having the first specific wavelength transmitted through the first light band-pass filter is sensed by the first photosensor and the light having second specific wavelength transmitted through the second light band-pass filter is sensed by the second photosensor. Thereby, downsizing of the spectroscopic sensor device or the like may be realized.

Further, in another aspect of the invention, the spectroscopic sensor device may include a light blocking member that blocks the light entering the spectroscopic sensor from the light source unit not via the object of observation when a reflected light obtained by application of the light from the light source unit to the object of observation enters the spectroscopic sensor.

In this case, the light entering the spectroscopic sensor from the light source unit not via the object of observation may be blocked, and the reflected light obtained by application of the light from the light source unit to the object of observation may be allowed to enter the spectroscopic sensor.

Furthermore, in another aspect of the invention, the light source unit may apply the light across a facing surface that faces the object of observation, the spectroscopic sensor may receive the light entering across the facing surface, and the light blocking member may be provided between the light source unit and the spectroscopic sensor.

In this case, the light blocking member is provided between the light source unit and the spectroscopic sensor, and thereby, the light entering the spectroscopic sensor from the light source unit not via the object of observation may be blocked.

In addition, in another aspect of the invention, the plural photosensor parts may be arranged in an array at a first direction side of the light source unit in a plan view with respect to the facing surface that faces the object of observation.

In this case, the plural photosensor parts are arranged in the array at the first direction side of the light source unit, and thereby, the reflected lights obtained by the application of the light from the light source unit to the object of observation may be allowed to enter the spectroscopic sensor.

Further, in another aspect of the invention, the plural photosensor parts may be arranged around the light source unit in a plan view with respect to the facing surface that faces the object of observation.

In this case, the plural photosensor parts are arranged around the light source unit, and thereby, the reflected light obtained by the application of the light from the light source unit to the object of observation may be allowed to enter the spectroscopic sensor.

Furthermore, in another aspect of the invention, the light source unit may be arranged around the plural photosensor parts in a plan view with respect to the facing surface that faces the object of observation.

In addition, in another aspect of the invention, the light source unit includes plural light sources, and the plural light sources are arranged around the plural photosensor parts in a plan view with respect to the facing surface that faces the object of observation.

In this case, the light source unit is arranged around the plural photosensor parts, and thereby, the reflected lights obtained by the application of the light from the light source unit to the object of observation may be allowed to enter the spectroscopic sensor.

Further, in another aspect of the invention, the spectroscopic sensor device may include an angle limiting filter for limiting incident angles of incident lights to light receiving areas of the plural photosensor parts.

In this case, since the incident angles of incident lights to the light receiving areas of the plural photosensor parts are limited, the transmission wavelength bands of the plural light band-pass filters may be limited. Further, the light entering the spectroscopic sensor from the light source unit not via the object of observation may be blocked.

Furthermore, in another aspect of the invention, the angle limiting filter may be formed by a light blocking material formed on impurity regions for the plural photosensor parts using a semiconductor process.

In this case, the light blocking material may be formed on the impurity regions for the plural photosensor parts using the semiconductor process.

In addition, in another aspect of the invention, the angle limiting filter may be formed at a wiring layer forming step of another circuit formed on a semiconductor substrate.

In this case, the angle limiting filter may be formed at the wiring layer forming step of the other circuit formed on the semiconductor substrate.

Further, in another aspect of the invention, the angle limiting filter may be formed by a conducting plug of a contact hole provided in an insulating film stacked on the semiconductor substrate.

In this case, the angle limiting filter may be formed by the conducting plug of the contact hole provided in the insulating film stacked on the semiconductor substrate.

Furthermore, in another aspect of the invention, the light blocking material forming the angle limiting filter may be a light absorbing material or a light reflecting material.

In this case, the light blocking material forming the angle limiting filter may be formed by the light absorbing material or the light reflecting material.

In addition, in another aspect of the invention, the angle limiting filter may be formed using the semiconductor substrate left after formation of holes for receiving lights towards the impurity regions for the plural photosensor parts from a rear surface side of the semiconductor substrate when the surface on which the impurity regions for the plural photosensor parts are formed is a front surface of the semiconductor substrate.

In this case, the angle limiting filter may be formed using the semiconductor substrate left after formation of the holes for receiving lights towards the impurity regions for the plural photosensor parts from the rear surface side of the semiconductor substrate.

Further, in another aspect of the invention, the plural light band-pass filters may be formed by multilayer thin films tilted at angles in response to the transmission wavelengths relative to the semiconductor substrate.

In this case, the plural light band-pass filters may be formed by multilayer thin films tilted at the angles in response to the transmission wavelengths relative to the semiconductor substrate.

Furthermore, in another aspect of the invention, the spectroscopic sensor device may include a tilted structure provided on the angle limiting filter, wherein the tilted structure has tilted surfaces at angles in response to the transmission wavelengths of the plural light band-pass filters relative to the semiconductor substrate, and the multilayer thin films are formed on the tilted surfaces.

In this case, the multilayer thin films are formed on the tilted surfaces of the tilted structure, and thereby, the multilayer thin films tilted at the angles in response to the transmission wavelengths may be formed.

In addition, in another aspect of the invention, the light blocking material may be provided on the rear surface of the semiconductor substrate left after formation of the holes for receiving lights and wall surfaces of the holes for receiving lights.

In this case, the light blocking material may be provided on the rear surface of the semiconductor substrate left after formation of the holes for receiving lights and side surfaces of the holes for receiving lights.

Further, in another aspect of the invention, the light blocking material may be a light absorbing material or a light reflecting material.

In this case, the light blocking material may be formed by the light absorbing material or the light reflecting material.

Furthermore, still another aspect of the invention relates to electronic equipment including the spectroscopic sensor device according to the above aspect.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail. Note that the embodiments described as below do not unduly limit the subject matter of the invention described in claims, and all of the configurations explained in the embodiments are not necessarily essential as solving means of the invention.

1. Configuration Example

As described above, in medical, health fields or the like, small spectroscopic sensor devices that are constantly wearable are required, and there is a task of requiring downsizing of the spectroscopic sensor devices. In the embodiment, downsizing of the spectroscopic sensor device is realized by measuring a specific wavelength band using a light band-pass filter.

Figure 1A:
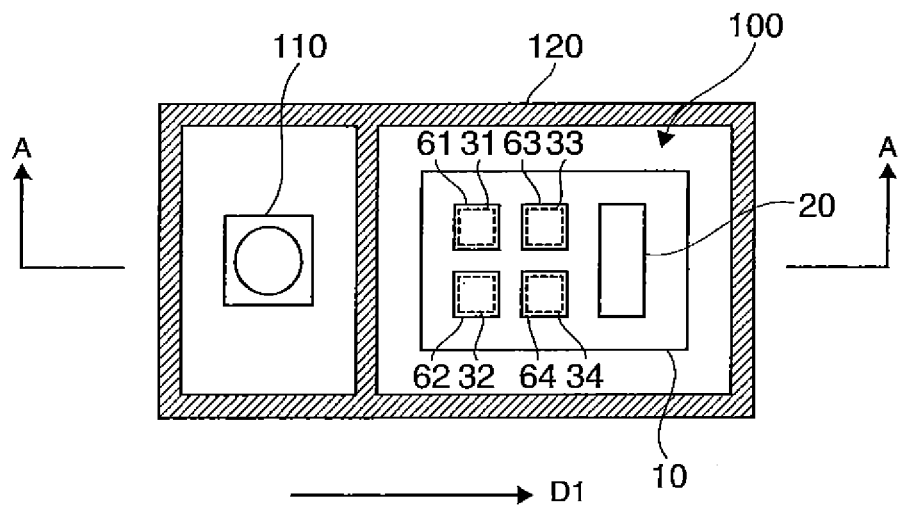
FIGS. 1A and 1B show a configuration example of a spectroscopic sensor device of the embodiment.
Figure 1B:
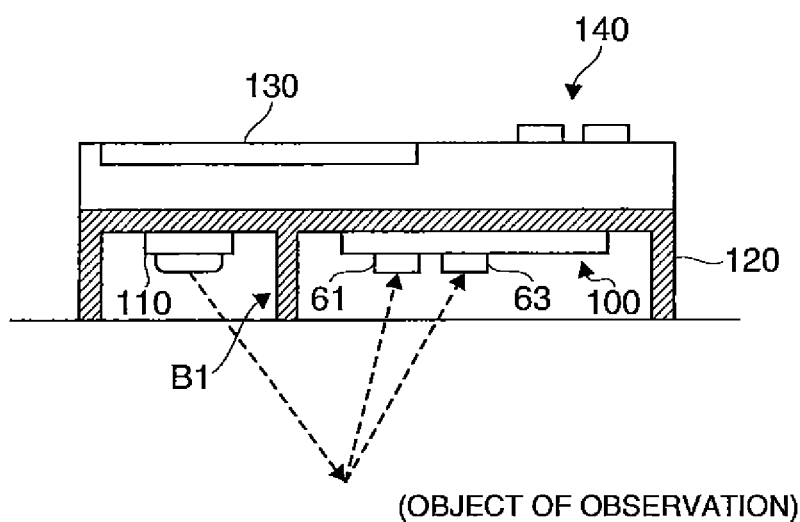

FIGS. 1A and 1B show a configuration example of a spectroscopic sensor device of the embodiment. The spectroscopic sensor device of the embodiment includes a spectroscopic sensor 100, a light source 110, a light blocking member 120, a display panel 130 (display device), and an operation input unit 140. As below, the configuration of the spectroscopic sensor device is schematically shown for simplicity, and the dimensions and ratios in the drawings are different from those of the real one.

FIG. 1A is a plan view of a facing surface that faces an object of observation. As shown in FIG. 1A, the light source 110 and the spectroscopic sensor 100 are respectively surrounded by the light blocking member 120. The light blocking member 120 blocks the direct light from the light source 110 to the spectroscopic sensor 100, and blocks the outside light of sun light, illumination light, or the like. The light blocking member 120 is realized by plastic or metal, for example, and formed using an opaque material that does not transmit a wavelength as a target of measurement of the spectroscopic sensor 100.

The light source 110 includes an LED, for example, and applies a light in a broad wavelength band to the object of observation. The light in the wide wavelength band is white light, for example, and a light in a wide range (e.g., several hundreds of nanometers) containing a wavelength to be measured in a narrow range (e.g., several tens of nanometers) of the spectroscopic sensor 100. Note that, as will be described later, the light source 110 may include plural light sources and the respective light sources may apply lights having different measurement wavelengths.

The spectroscopic sensor 100 is formed on one chip of semiconductor substrate, for example, and spectroscopically measures (detects) light in a specific wavelength band. Specifically, the spectroscopic sensor 100 includes a semiconductor substrate 10, a circuit 20, first to fourth photodiodes 31 to 34 (plural photosensor parts in abroad sense), and first to fourth light band-pass filters 61 to 64 (first to fourth multilayer thin-film filters).

The photodiodes 31 to 34 are devices formed on the semiconductor substrate 10 for photoelectrically converting incident lights. The photodiodes 31 to 34 receive the incident lights respectively transmitted through the light band-pass filters 61 to 64.

The light band-pass filters 61 to 64 are optical filters realized by multilayer thin films formed on the photodiodes 31 to 34, for example, and transmit light in specific wavelength bands. The specific wavelength bands contain plural bands to be measured and the respective light band-pass filters transmit the lights in the respective bands to be measured. For example, the respective bands to be measured are bands of several tens of nanometers containing measurement wavelengths.

FIG. 1B is a sectional view along A-A of the spectroscopic sensor device shown in FIG. 1A. As shown in FIG. 1B, when the spectroscopic sensor device is used, the end surface (facing surface) of the light blocking member 120 is in contact with the object of observation. Both the light source 110 and the spectroscopic sensor 100 are provided to face the object of observation. Further, the light from the light source 110 is applied to the object of observation and the reflected light or the scattered light from the object of observation enters the spectroscopic sensor 100.

As shown by B1, the light blocking member 120 includes a member provided between the light source 110 and the spectroscopic sensor 100. The member has a plate-like shape, for example, and is provided to intersect with a line connecting the light source and the spectroscopic sensor 100 (the light receiving surfaces of the photodiodes). Further, one side of the member is in contact with the object of observation in use, and the direct light from the light source 110 to the spectroscopic sensor 100 is blocked.

The configuration of the spectroscopic sensor device of the embodiment is not limited to that of FIGS. 1A and 1B, and various changes may be made by omitting part of its component elements (e.g., the display panel 130, the input unit 140), or adding other component elements (e.g., an input/output interface).

As described above, in the spectroscopic sensor device, there is a requirement of downsizing of the device. For example, in a spectroscopic sensor that acquires a continuous spectrum, there is a problem that the device is upsized by providing a prism etc. and securing an optical path length.

In this regard, according to the embodiment, the spectroscopic sensor device includes the light source unit 110 that applies the light in a wavelength band containing plural wavelengths as targets of detection, and the spectroscopic sensor 100 into which the light obtained by application of the light from the light source unit 110 to the object of observation enters. The spectroscopic sensor 100 has the plural light band-pass filters 61 to 64 having different transmission wavelengths and the plural photosensor parts 31 to 34. For example, the first light band-pass filter 61 has a wavelength characteristic of transmitting a first specific wavelength and the first photosensor 31 senses the light having the first specific wavelength transmitted through the first light band-pass filter 61. The second light band-pass filter 62 has a wavelength characteristic of transmitting a second specific wavelength different from the first specific wavelength, and the second photosensor 32 senses the light having the second specific wavelength transmitted through the second light band-pass filter 62.

Thereby, downsizing of the spectroscopic sensor device or the like may be realized. That is, only the specific wavelengths are spectroscopically measured using the light band-pass filters 61 to 64, and thus, it becomes unnecessary to provide a prism or the like or secure the optical path length, and the device may be downsized. Generally, in a spectroscopic sensor device for specific use, the wavelength to be measured is known, and acquirement of the continuous spectrum like in analysis use is not necessarily required.

Accordingly, only the specific wavelengths may be measured according to the technique, and the device may be downsized.

Here, the object of observation is an object of spectroscopic measurement by the spectroscopic sensor device, and, for example, skin, subcutaneous tissues, blood of a human, a liquid of seawater or the like, agricultural products of fruits or the like, soil, etc. are assumed.

Note that the light obtained by application of the light from the light source unit 110 to the object of observation may be reflected light or scattered light from the object of observation as described above, and, as will be described in FIG. 5, it may be the transmitted light transmitted through the object of observation.

Further, the embodiment includes the light blocking member 120 that blocks the light entering the spectroscopic sensor 100 from the light source unit 110 not via the object of observation in the case where the reflected light obtained by application of the light from the light source unit 110 to the object of observation enters the spectroscopic sensor 100.

More specifically, the light source unit 110 applies illumination light across the facing surface that faces the object of observation, and the spectroscopic sensor 100 receives the reflected light or the scattered light from the object of observation entering across the facing surface. Further, the light blocking member 120 is provided between the light source unit 110 and the spectroscopic sensor 100.

For example, as described above in FIG. 1B, the light source unit 110 and the spectroscopic sensor 100 are provided adjacent to each other and the light blocking member (the part shown by B1) is provided to block the direct light from the light source unit 110 to the spectroscopic sensor 100. Alternatively, as will be described later in FIGS. 2A and 2B, the spectroscopic sensor 100 may be provided around the light source unit 110 and a light blocking member 121 may be provided to surround the light source 110.

According to the configuration, the light entering the spectroscopic sensor 100 from the light source unit 110 not via the object of observation may be blocked and only the reflected light or scattered light from the object of observation may be spectroscopically separated. Thereby, S/N deterioration due to direct light may be suppressed.

Here, the above described facing surface is a surface assumed to face the object of observation in use of the spectroscopic sensor device. For example, as shown in FIG. 1B, in the case where the end surface of the light blocking member 120 is formed in contact with the object of observation, the surface containing the end surface is the facing surface.

Further, in the embodiment, the plural photosensor parts 31 to 34 of the spectroscopic sensor 100 are provided in an array at the first direction side of the light source unit 110 in a plan view with respect to the facing surface that faces the object of observation. For example, in FIG. 1A, the first direction is a direction shown by D1 and the plural photosensor parts 31 to 34 are provided at a certain direction D1 side not around the light source unit 110.

Furthermore, as will be described later in FIGS. 2A and 2B, the plural photosensor parts 31 to 34 may be provided around the light source unit 110 in the plan view with respect to the facing surface that faces the object of observation.

Figure 3:
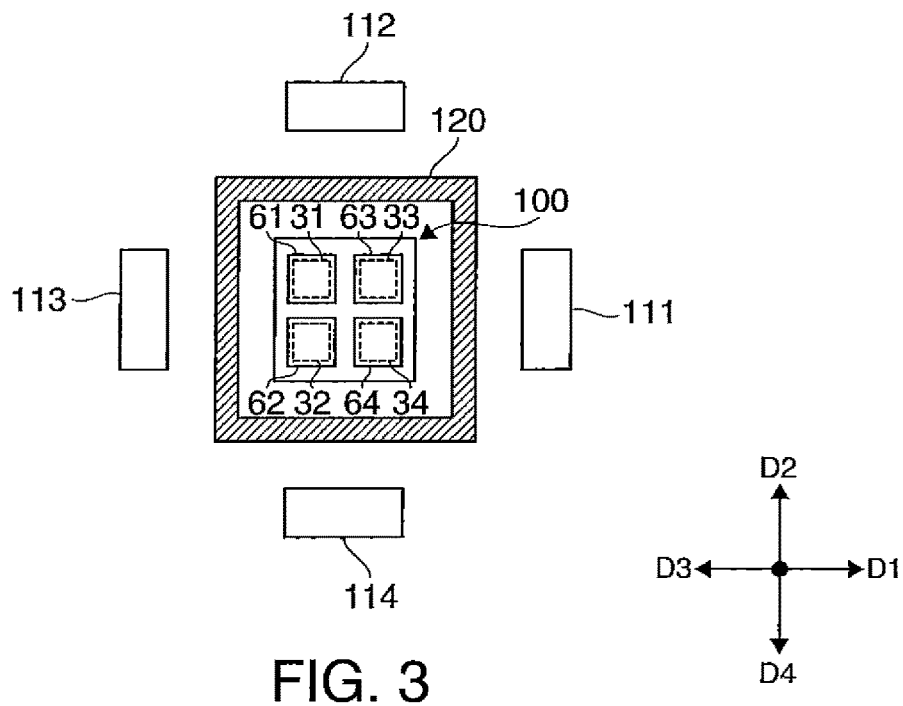
FIG. 3 shows a second modified example of the spectroscopic sensor device.
Figure 4:
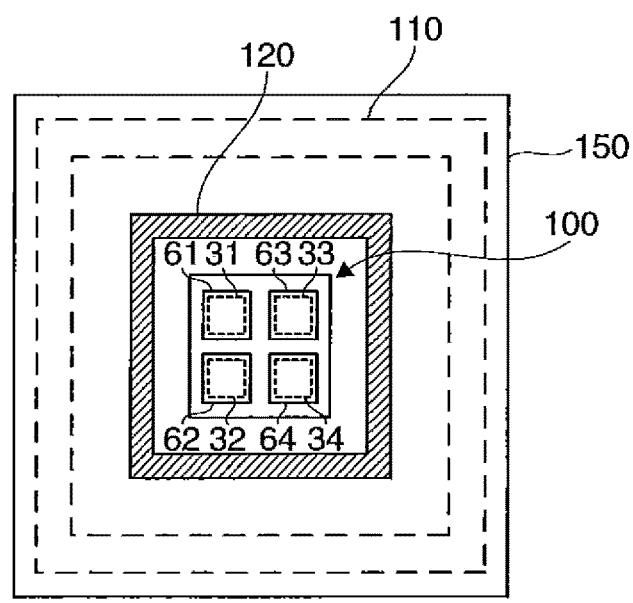
FIG. 4 shows a third modified example of the spectroscopic sensor device.

In addition, as will be described later in FIGS. 3 and 4, the light source unit 110 may be provided around the plural photosensor parts 31 to 34 in the plan view with respect to the facing surface that faces the object of observation. For example, as shown in FIG. 3, the light source unit 110 may include plural light sources 111 to 114 and the plural light sources 111 to 114 may be provided around the plural photosensor parts 31 to 34. Alternatively, as shown in FIG. 4, the light source unit 110 may include one light source and the one light source may be provided around the plural photosensor parts 31 to 34.

According to these embodiments, the light source unit 110 and the spectroscopic sensor 100 may compactly be provided and the spectroscopic sensor device may be downsized. Further, in the case where the light source unit 110 may be provided around the plural photosensor parts 31 to 34, the spectroscopic sensor 100 may be provided farther away from the outside light and the S/N deterioration due to outside light may be suppressed.

2. Modified Examples

As already mentioned, various modified configurations may be made for the spectroscopic sensor device of the embodiment. Using FIGS. 2A to 5, various modified examples of the spectroscopic sensor device will be explained.

Figure 2A:
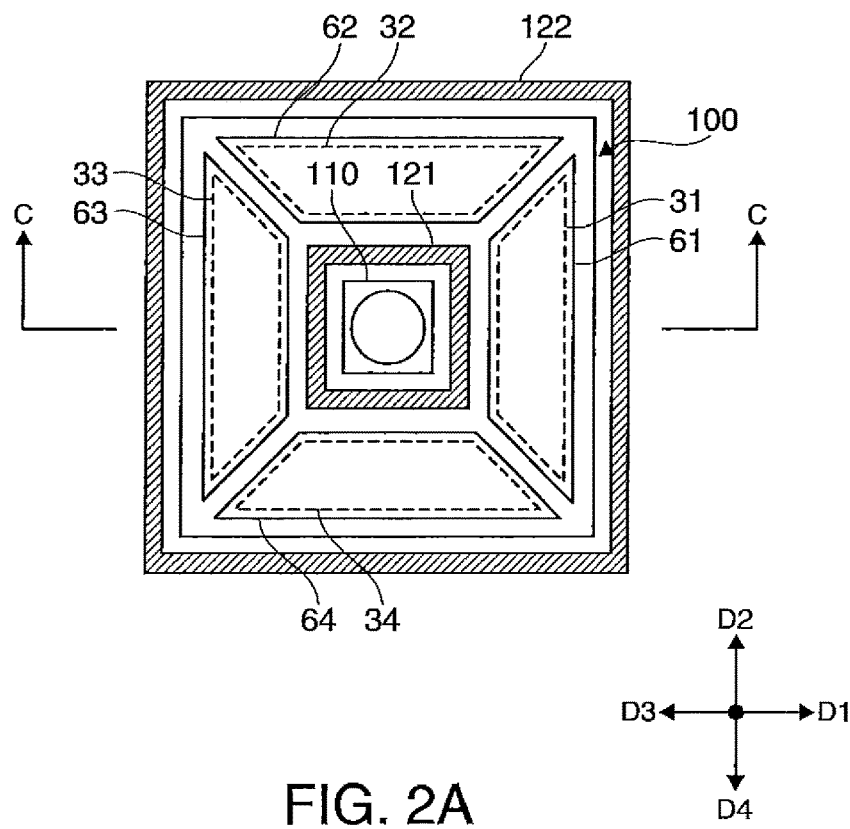
FIGS. 2A and 2B show a first modified example of the spectroscopic sensor device.
Figure 2B:
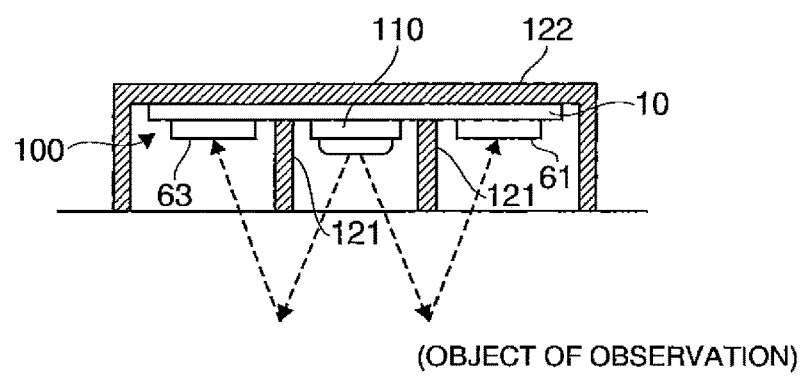

FIGS. 2A and 2B show a first modified example of the spectroscopic sensor device in which photodiodes are provided around the light source unit. The spectroscopic sensor device includes a spectroscopic sensor 100, a light source unit 110, and light blocking members 121, 122.

FIG. 2A is a plan view of a facing surface that faces an object of observation. As shown in FIG. 2A, the light blocking member 121 is provided to surround the light source unit 110, and plural photodiodes 31 to 34 are provided outside of the light blocking member 121. For example, the photodiodes 31 to 34 are provided at sides in the first to fourth directions D1 to D4 of the light source unit 110. Here, in a plan view with respect to the facing surface, D2 is a direction orthogonal to D1, D3 is a direction opposite to D3, and D4 is a direction opposite to D2. Further, the light blocking member 122 for blocking outside light is provided around the photodiodes 31 to 34.

FIG. 2B is a sectional view along C-C of the spectroscopic sensor device shown in FIG. 2A. As shown in FIG. 2B, the light source unit 110 and the light blocking member 121 are provided (stacked) on the semiconductor substrate 10 on which the photodiodes 31 to 34 are formed. In an area on the semiconductor substrate 10 where the light source unit 110 is provided, for example, a driver circuit for the light source 110 and detection circuits for the photodiodes 31 to 34 are formed. Here, "on the semiconductor substrate 10" refers to directions perpendicular to the plane of the semiconductor substrate 10 and at the sides at which the photodiodes 31 to 34, the light band-pass filters 61 to 64, etc are formed.

FIG. 3 shows a second modified example of the spectroscopic sensor device in which plural light sources are provided around the spectroscopic sensor 100. The spectroscopic sensor device includes a spectroscopic sensor 100, first to fourth light sources 111 to 114 (plural light sources in a broad sense), and a light blocking member 120.

As shown in FIG. 3, the light blocking member 120 is provided to surround the spectroscopic sensor 100, and the light sources 111 to 114 are provided outside of the light blocking member 120. For example, the light sources 111 to 114 are provided at sides in first to fourth directions D1 to D4 of the spectroscopic sensor 100. For example, in the case where the respective transmission wavelengths of the light band-pass filters 61 to 64 are contained in visible light, the light sources 111 to 114 apply white light to the object of observation. Alternatively, the light sources 111 to 114 may respectively apply lights in different wavelength bands corresponding to the transmission wavelengths of the light band-pass filters 61 to 64.

FIG. 4 shows a third first modified example of the spectroscopic sensor device in which one light source surrounds the spectroscopic sensor 100. The spectroscopic sensor device includes a spectroscopic sensor 100, a light source unit 110, and a light blocking member 120.

As shown in FIG. 4, the light blocking member 120 is provided to surround the spectroscopic sensor 100, and the light source 110 as one piece having a rectangular shape, a circular shape, or the like surrounding the outside of the light blocking member 120 is provided. The light source 110 is realized using an EL (Electro-Luminescence) that radiates white light or the like, for example, and formed on an EL substrate 150. The spectroscopic sensor 100 is provided to be stacked on the EL substrate, for example.

Figure 5:
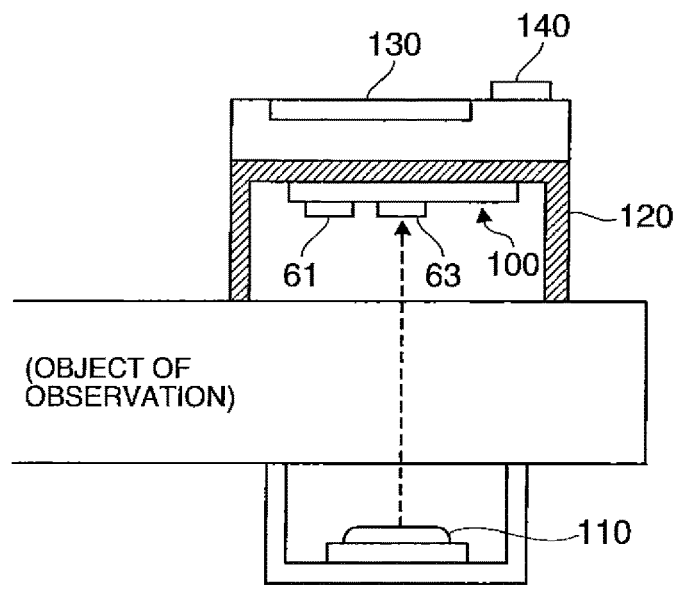
FIG. 5 shows a fourth modified example of the spectroscopic sensor device.

FIG. 5 shows a fourth modified example of the spectroscopic sensor device that spectroscopically measures transmitted light of an object of observation. The spectroscopic sensor device includes a spectroscopic sensor 100, a light source unit 110, a light blocking member 120, a display panel 130, and an operation input unit 140.

As shown in FIG. 5, the light source unit 110 and the spectroscopic sensor 100 are provided to be opposed with the object of observation in between in use of the spectroscopic sensor device. That is, the light source unit 110 applies illumination light to the object of observation, the illumination light transmitted through the object of observation enters the spectroscopic sensor 100, light band-pass filters 61, 63 spectroscopically separate the transmitted light, and photodiodes (not shown) sense the spectroscopically separated transmitted light.

3. First Detailed Configuration Example of Spectroscopic Sensor

As described above, using a spectroscopic sensor that measures not a continuous spectrum but only a specific measurement wavelength, the spectroscopic sensor device may be downsized. However, there is a problem that the size of the spectroscopic sensor device is restricted according to the size of the spectroscopic sensor itself.

However, there is a task of improving wavelength selectivity of the spectroscopic sensor. For example, as will be described later, in the spectroscopic sensor of the embodiment, an angle limiting filter for limiting the transmission wavelength band of the light band-pass filter is provided. In this regard, if the angle limiting filter and the light band-pass filter are formed in members, the light is diffused and attenuated on the bonded surfaces of the members, and the wavelength selectivity becomes lower.

Further, for example, in the above described Patent Document 1, a technique of limiting the transmission wavelength band of a filter by limiting the incident angle of incident light using an optical fiber is disclosed. However, according to the technique, if the numerical aperture of the optical fiber is made smaller for narrowing the band, the transmittance of the incident light becomes lower and the wavelength selectivity becomes lower.

Furthermore, there is a task of simplifying the manufacturing process of the spectroscopic sensor. For example, in Patent Document 2, a technique using multilayer filters having different film thicknesses with respect to each sensor is disclosed. However, according to the technique, separate multilayer film forming steps are necessary with respect to each film thickness, and the forming steps of the multilayer films become complex.

Accordingly, in the embodiment, downsizing of the spectroscopic sensor is realized in a simple manufacturing process by forming an angle-limiting filter and a light band-pass filter using a semiconductor process.

A first detailed configuration example of the spectroscopic sensor will be explained using FIGS. 6, 7. As below, the configuration of the spectroscopic sensor will be schematically shown for simplicity, and the dimensions and ratios in the drawings are different from those of the real one.

Figure 6:
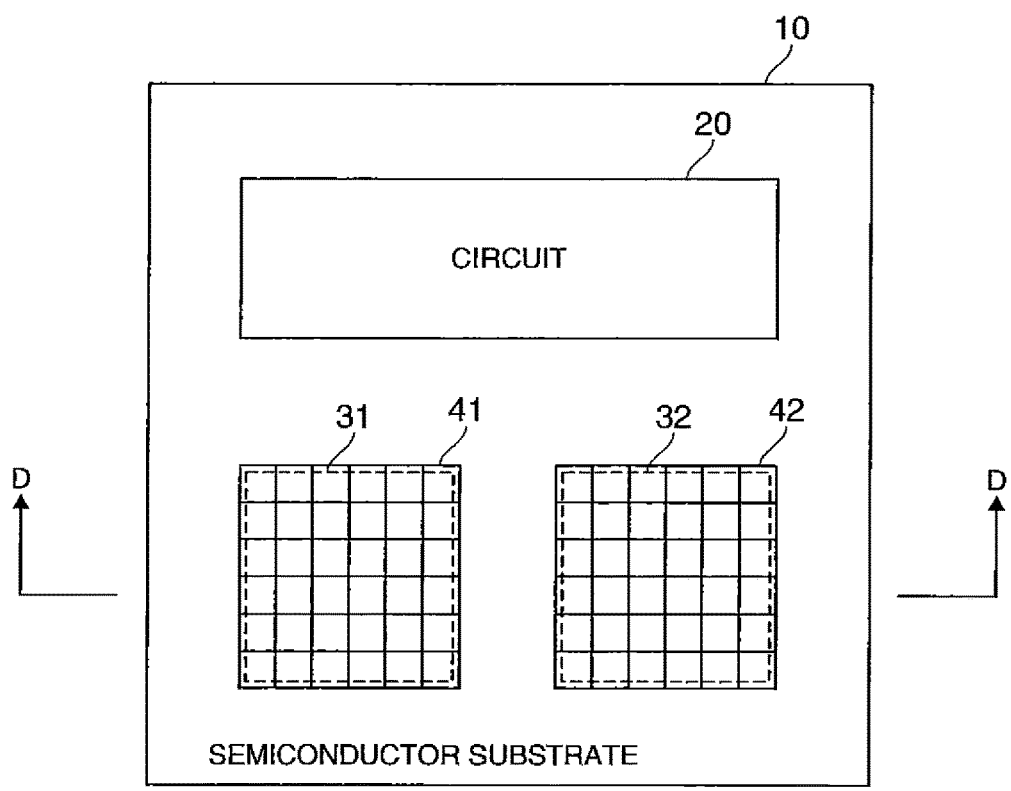
FIG. 6 shows a first detailed configuration example of a spectroscopic sensor.

FIG. 6 is a plan view with respect to the semiconductor substrate 10 on which the spectroscopic sensor is formed. FIG. 6 is the plan view seen from the front side on which a circuit 20, an angle limiting filter 41, etc. are formed in the plan view seen from a direction perpendicular to the plane of the semiconductor substrate 10. As will be described later, multilayer filters are formed on the angle limiting filters 41, 42, however, in FIG. 6, they are not shown for simplicity.

The spectroscopic sensor shown in FIG. 6 includes the semiconductor substrate 10, the circuit 20, a first photodiode 31 (an impurity region for a first photosensor and the first photodiode in a broad sense), a second photodiode 32 (an impurity region for a second photosensor and the second photodiode in a broad sense), the first angle limiting filter 41, and the second angle limiting filter 42.

The semiconductor substrate 10 includes a P-type or N-type silicon substrate (silicon wafer), for example. On the semiconductor substrate 10, the circuit 20, the photodiodes 31, 32, and the angle limiting filters 41, 42 are formed using a semiconductor process. Here, "on the semiconductor substrate 10" refers to directions at the sides at which the circuit 20, the angle limiting filter 41, etc. are formed of the directions perpendicular to the plane of the semiconductor substrate 10.

The angle limiting filters 41, 42 are formed in lattice forms in a plan view, for example, and limit the incident angles of incident lights to the photodiodes 31, 32. The circuit 20 includes amplifiers that process output signals from the photodiodes 31, 32, A/D conversion circuits, etc., for example.

Note that the configuration of the spectroscopic sensor in the embodiment is not limited to that of FIG. 6, and various changes may be made by omitting part of its component elements (e.g., the circuit 20), or adding other component elements. For example, the numbers of photodiodes and angle limiting filters may be two as described above, or may be one or more. Further, the angle limiting filters 41, 42 may have lattice forms in the plan view as described above, or other forms.

Figure 7:
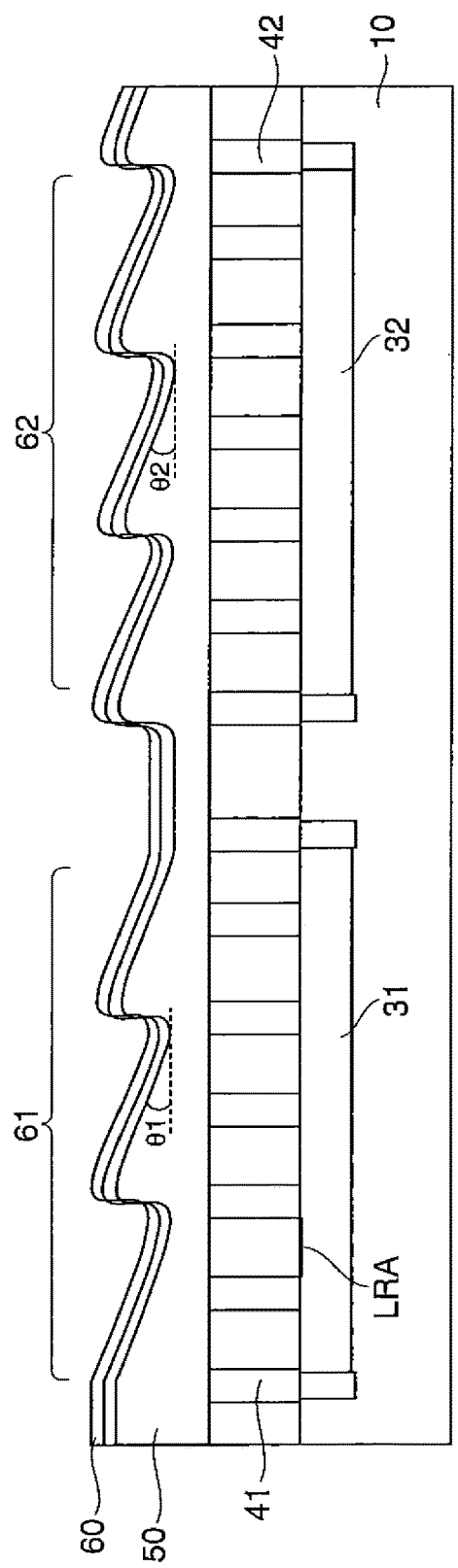
FIG. 7 shows the first detailed configuration example of the spectroscopic sensor.

FIG. 7 shows a sectional view of the spectroscopic sensor. FIG. 7 is the sectional view along D-D section shown in FIG. 6. The spectroscopic sensor shown in FIG. 7 includes a semiconductor substrate 10, photodiodes 31, 32, angle limiting filters 41, 42, a tilted structure 50 (angular structure), a first light band-pass filter 61 (a first multilayer filter, a first dielectric filter), and a second light band-pass filter 62 (a second multilayer filter, a second dielectric filter).

As shown in FIG. 7, the photodiodes 31, 32 are formed on the semiconductor substrate 10. As will be described later, the photodiodes 31, 32 are formed by forming impurity regions using ion implantation or the like. For example, the photodiodes 31, 32 are realized by P-N junction between an N-type impurity region formed on a P-substrate and the P-substrate. Alternatively, they are realized by P-N junction between a P-type impurity region formed on a deep N-well (N-type impurity region) and the deep N-well.

The angle limiting filters 41, 42 are formed using a light blocking material having a light blocking property (a light absorbing material or a light reflecting material) with respect to wavelengths detected by the photodiodes 31, 32. Specifically, the angle limiting filters 41, 42 are formed at wiring forming steps of the semiconductor process and formed by a conducting layer of an aluminum (light reflecting material) wiring layer or a conducting plug of tungsten (light absorbing material) plug or the like, for example. The aspect ratios of the lengths of the bottom sides (e.g., the longest diagonal lines of the bottom surfaces or the longer diameters) to the heights of the angle limiting filters 41, 42 are set in response to the transmission wavelength bands of the light band-pass filters 61, 62 (e.g., BW1, BW2, which will be described later in FIG. 12B). The opening parts (hollow parts) of the angle limiting filters 41, 42 are formed using transparent materials with respect to wavelengths detected by the photodiodes 31, 32, and, for example, formed (filled) by insulating layers of $SiO_2$ (silicon oxide films) or the like.

The tilted structure 50 is formed on the angle limiting filters 41, 42 and has tilted surfaces at different tilt angles in response to the transmission wavelengths of the light band-pass filters 61, 62. Specifically, on the photodiode 31, plural tilted surfaces at a tilt angle $\theta 1$ relative to the plane of the semiconductor substrate 10 are formed, and, on the photodiode 32, plural tilted surfaces at a tilt angle $\theta 2$ different from the tilt angle $\theta 1$ are formed. As will be described later, the tilted structure 50 is formed by processing the insulating films of $SiO_2$ or the like, for example, by etching, CMP, a gray scale lithography technology, or the like.

The light band-pass filters 61, 62 are formed by a multi-layer thin film 60 stacked on the tilted structure 50. The transmission wavelength bands of the light band-pass filters 61, 62 are determined by the tilt angles $\theta 1$, $\theta 2$ of the tilted structure 50 and incident light limited angles (aspect ratios) of the angle limiting filters 41, 42. The light band-pass filters 61, 62 have configurations by which transmission wavelengths vary in response to the tilt angles, and are not stacked at separate steps with respect to each transmission wavelength but stacked at the same multilayer film forming steps.

As described above, for downsizing the spectroscopic sensor device, there is a task of requiring of downsizing of the spectroscopic sensor. Further, there are tasks of improving wavelength selectivity of the spectroscopic sensor and simplifying the manufacturing process.

In this regard, according to the embodiment, the spectroscopic sensor includes the angle limiting filters 41, 42 for limiting the incident angles of incident lights to the light receiving areas (light receiving surfaces) of the photodiodes. Further, the angle limiting filters 41, 42 are formed using a light blocking material (a light absorbing material or a light reflecting material) formed using a semiconductor process on the impurity regions for the photodiodes 31, 32.

Thereby, the respective component elements of the spectroscopic sensor may be formed using the semiconductor process, and downsizing of the spectroscopic sensor or the like may be realized. That is, by forming the photodiodes 31, 32 and the angle limiting filters 41, 42 using the semiconductor process, microfabrication may be easily performed and downsizing may be realized. Further, compared to the case where the configuration is formed by bonding members, the manufacturing process may be simplified. Furthermore, compared to the case of using optical fibers as angle limiting filters, reduction of transmitted lights due to the reduction of limited angles (numerical apertures) may be suppressed. In addition, reduction of transmitted lights due to bonding of members may be suppressed. Accordingly, the amounts of lights may be easily secured, and the transmission wavelength bands may be made smaller by making the limited angles smaller.

Here, the semiconductor process refers to a process of forming transistors, resistance elements, capacitors, insulating layers, wiring layers, etc. on a semiconductor substrate. For example, the semiconductor process includes an impurity introduction process, a thin film formation process, a photolithography process, an etching process, a planarization process, and a thermal treatment process.

Further, the light receiving areas of the photodiodes refer to areas on the impurity regions for the photodiodes 31, 32 into which incident lights that have passed through the angle limiting filters 41, 42 enter. For example, in FIG. 6, they are area corresponding to the respective openings of the lattice-formed angle limiting filters 41, 42. Alternatively, in FIG. 7, they are areas (for example, areas LRA) surrounded by the light blocking material (the light absorbing material or the light reflecting material) forming the angle limiting filters 41, 42.

Further, in the embodiment, the angle limiting filters 41, 42 are formed at the wiring layer forming steps of another circuit 20 formed on the semiconductor substrate 10. Specifically, the angle limiting filters 41, 42 are formed at the same time with the wiring layer formation of the circuit 20 and formed at all or part of the wiring layer forming steps. For example, the angle limiting filters 41, 42 are formed by aluminum (a light reflecting material in a broad sense) wiring layer formation using aluminum sputtering, insulating film formation using $SiO_2$ deposition, contact formation using tungsten (a light absorbing material in a broad sense) deposition, or the like.

In this manner, the angle limiting filters 41, 42 may be formed using the semiconductor process on the impurity regions for the photodiodes 31, 32. Thereby, it is not necessary to provide a separate process for formation of the angle limiting filters, and the angle limiting filters may be formed using a normal semiconductor process.

Note that the angle limiting filters 41, 42 may be formed not only by the aluminum (light reflecting material) wiring layers or the tungsten (light absorbing material) contacts but also by wiring layers using a light absorbing material of tungsten or the like or contacts using a light reflecting material of aluminum or the like. However, the light blocking property becomes higher, as the amount of the light absorbing material is larger.

Further, the angle limiting filters 41, 42 may be formed not only by the aluminum (light reflecting material) wiring layers or the tungsten (light absorbing material) contacts but also by aluminum (light reflecting material) wiring layers or tungsten (light absorbing material) contacts with films of titanium nitride (TiN) or the like as a light absorbing material. The property of the aluminum (light reflecting material) wiring layers change to a light absorption property and the light absorption of titanium nitride (TiN) is higher than tungsten, and the light absorption of the contacts becomes higher and the light blocking property may be further improved.

Furthermore, in the embodiment, the angle limiting filters 41, 42 may be formed using conducting plugs for contact holes provided in the insulating films stacked on the semiconductor substrate 10. That is, they may be formed only using conducting plugs of tungsten (light absorbing material) plugs or the like formed in the insulating films of $SiO_2$ or the like without using metal wiring layers of aluminum (light reflecting material) wiring layers or the like. Note that the angle limiting filters 41, 42 may be formed not only by the tungsten plugs but also by other conducting plugs of aluminum, polysilicon, or the like.

In this case, the angle limiting filters 41, 42 may be formed using conducting plugs.

Here, the above described contact holes refer to contact holes provided for contacts for conduction between the wiring layers and the wiring layers, or contact holes provided for via contacts for conduction between the wiring layers and the semiconductor substrate.

Further, in the embodiment, the angle limiting filters 41, 42 may be electrodes that acquire signals from the impurity regions for the photodiodes 31, 32 formed using conducting layers or conducting plugs formed using the semiconductor process. For example, in the case where the impurity regions for the photodiodes 31, 32 are P-type impurity regions, the angle limiting filters 41, 42 in conduction with the P-type impurity regions may also serve as anode electrodes of the photodiodes 31, 32.

In this case, the angle limiting filters 41, 42 formed using conducting layers or conducting plugs may be used as the electrodes of the photodiodes 31, 32. Thereby, it is not necessary to provide electrodes other than the angle limiting filters 41, 42, and the reduction of the amounts of incident lights due to electrodes may be avoided.

In addition, in the embodiment, the angle limiting filters 41, 42 are formed along the outer circumferences of the light receiving areas of the photodiodes 31, 32 in the plan view with respect to the semiconductor substrate 10. Specifically, the impurity regions for the photodiodes 31, 32 are the respective one light receiving areas, and the respective one angle limiting filters to surround the outer circumferences of the impurity regions are formed. Alternatively, plural light receiving areas may be set in the impurity regions for the photodiodes 31, 32, and plural openings may be formed along the outer circumferences of the light receiving areas. For example, as shown in FIG. 6, square light blocking materials surround the respective light receiving areas in the plan view, and the squares are arranged in the lattice forms to form the angle limiting filters 41, 42.

Note that the angle limiting filters 41, 42 may not be limited to be closed along the outer circumferences of the light receiving areas, but may have discontinuous parts along the outer circumferences or be intermittently arranged along the outer circumferences.

In this case, the angle limiting filters 41, 42 are formed along the outer circumferences of the respective light receiving areas of the photodiodes 31, 32, and the incident angles of the incident lights to the respective light receiving areas of the photodiodes 31, 32 may be limited.

Further, in the embodiment, the light band-pass filters 61, 62 are formed using multilayer thin films tilted at the angles $\theta 1$, $\theta 2$ in response to the transmission wavelengths relative to the semiconductor substrate 10. More specifically, the light band-pass filters 61, 62 are formed using plural sets of multilayer thin films having different transmission wavelengths. Further, the plural sets of multilayer thin films have different tilt angles $\theta 1$, $\theta 2$ different in response to the transmission wavelengths relative to the semiconductor substrate 10 and are formed at a simultaneous thin film forming step. For example, as shown in FIG. 7, one set of multilayer thin films are formed by continuously arranging the plural multilayer thin films at the tilt angle $\theta 1$. Alternatively, as will be described later in FIG. 10, multilayer thin films having different tilt angle $\theta 1$ to $\theta 3$ may be provided adjacent to each other, and, in the case where the multilayer thin films having the tilt angle $\theta 1$ to $\theta 3$ are repeatedly provided, one set of multilayer thin films may be formed by plural multilayer thin films having the same tilt angle (e.g., $\theta 1$).

In this manner, the light band-pass filters 61, 62 may be formed using multilayer thin films tilted at the angles $\theta 1$, $\theta 2$ in response to the transmission wavelengths. Thereby, it is not necessary to stack the multilayer thin films having film thicknesses in response to the transmission wavelengths at separate step with respect to each transmission wavelength, and the forming step of the multilayer thin films may be simplified.

Here, the simultaneous thin film forming step refers not to a step of sequentially repeating the same step of forming a first set of multilayer thin films and then forming a second set of multilayer thin films, but to a step of forming plural sets of multilayer thin films at the same (simultaneous, single) thin film forming step.

Furthermore, in the embodiment, the spectroscopic sensor includes the tilted structure 50 provided on the angle limiting filters 41, 42. In addition, the tilted structure 50 has the tilted surfaces tilted at the angles $\theta 1$, $\theta 2$ in response to the transmission wavelengths of the light band-pass filters 61, 62 relative to the semiconductor substrate 10, and the multilayer thin films are formed on the tilted surfaces.

In this case, the multilayer thin films are formed on the tilted surfaces of the tilted structure 50, and the multilayer thin films tilted at the angles $\theta 1$, $\theta 2$ in response to the transmission wavelengths of the light band-pass filters 61, 62 may be formed.

Specifically, in the embodiment, the tilted structure 50 is formed on the angle limiting filters 41, 42 using the semiconductor process. For example, as will be described in FIG. 14 etc., the tilted structure 50 is formed by forming steps or a sparse and dense pattern on transparent films (insulating films) stacked using the semiconductor process, and performing at least one of grinding (e.g., CMP) and etching on the steps or the sparse and dense pattern.

In this manner, the tilted structure may be formed using the semiconductor process. Thereby, the forming step of the tilted structure may be simplified. Further, the cost may be reduced compared to the case where the tilted structure is formed using a separate member. Furthermore, the reduction of the amount of light on the bonded surface of the tilted structure as the separate member may be avoided.

Here, the steps of the insulating films are the level differences of the insulating film surfaces from the semiconductor substrate surface on the section of the semiconductor substrate. Further, the sparse and dense patterns of the insulating films are high and low patterns of the insulating film surfaces from the semiconductor substrate surface on the section of the semiconductor substrate, and the sparsity and density of the insulating films are formed according to the ratios of the higher parts and the lower parts.

Note that the tilted structure 50 may be formed not only by grinding or etching of the steps or the sparse and dense pattern, but using a gray scale lithography technology. In the gray scale lithography technology, the tilted structure is formed by exposing resists to light using a gray scale mask with dark and light parts, and performing etching using the exposed resists.

4. Modified Examples of Spectroscopic Sensor

In the embodiment, the configuration examples of forming the tilted structure 50 using the semiconductor process have been explained, and various modifications may be embodied in the embodiment.

Figure 8:
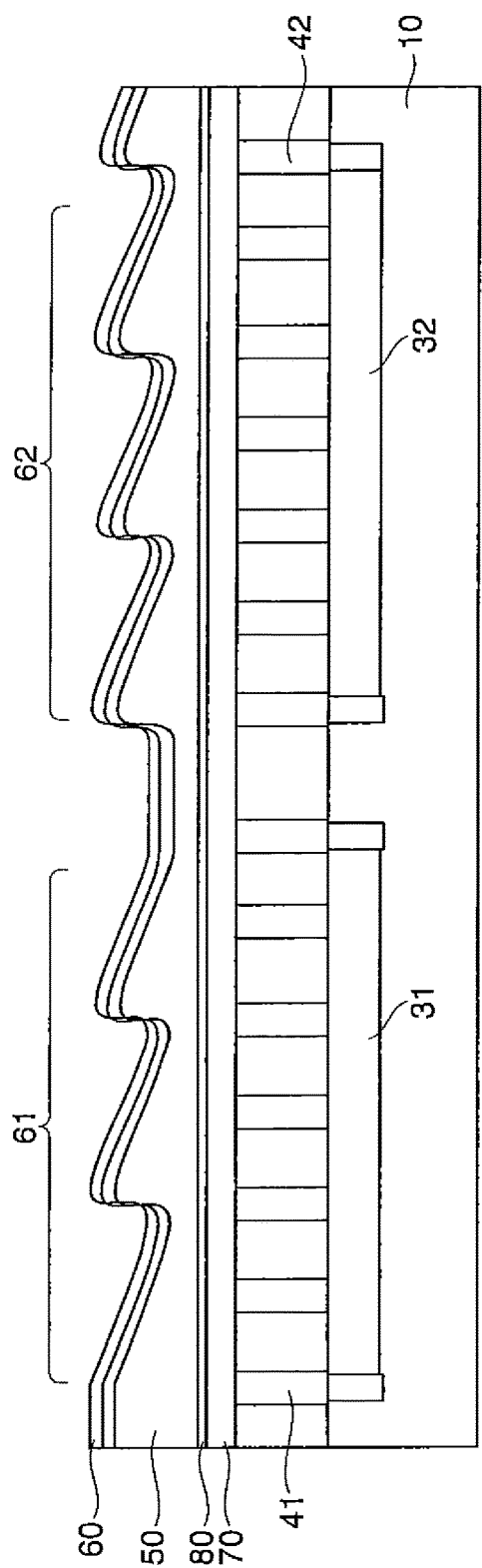
FIG. 8 shows a first modified example of the spectroscopic sensor.

FIG. 8 shows a first modified example of the spectroscopic sensor in which a tilted structure 50 is formed by a separate member and bonded. The spectroscopic sensor shown in FIG. 8 includes a semiconductor substrate 10, photodiodes 31, 32, angle limiting filters 41, 42, the tilted structure 50, light band-pass filters 61, 62, an insulating layer 70, and a bonding layer 80. As below, the same signs are assigned to the component elements described above in FIG. 7 etc., and their explanation will appropriately be omitted.

In the first modified example, the parts to the angle limiting filters 41, 42 are formed by the semiconductor process in the same manner as those of the above described configuration examples. The insulating layer 70 (or a passivation layer) is stacked on the angle limiting filters 41, 42. The insulating layer 70 is not necessarily an insulating film as long as it is a transparent film that transmits wavelengths to be sensed. The tilted structure 50 is formed by hot press of a separate member of low-melting-point glass or the like with a die, and tilted surfaces and multilayer thin films are formed thereon. The tilted structure 50 and the insulating layer 70 are bonded using a transparent adhesive that transmits wavelengths to be sensed.

Figure 9:
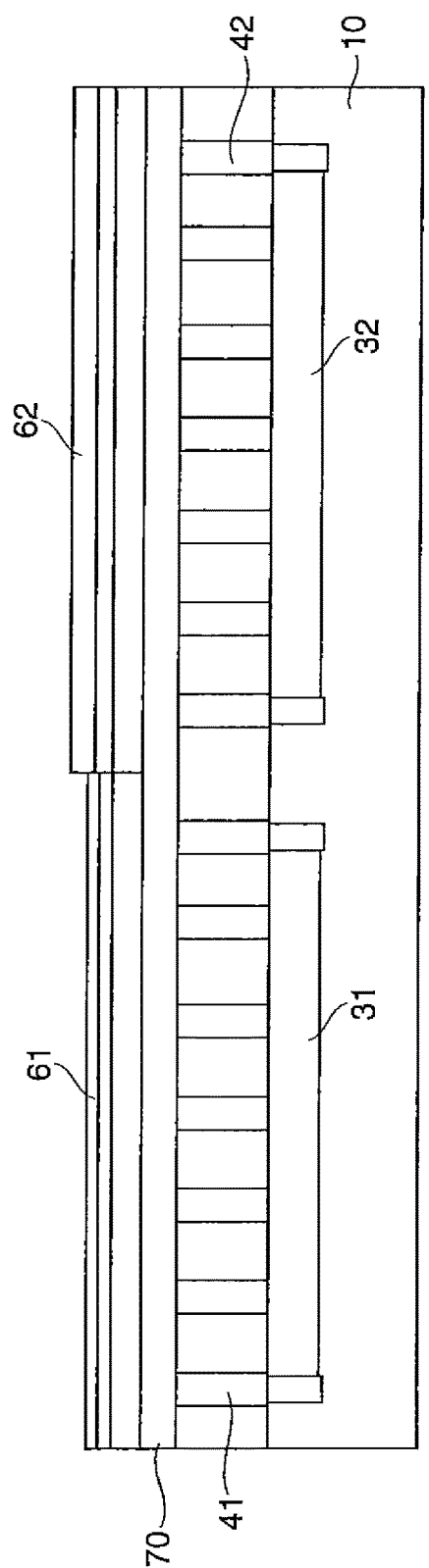
FIG. 9 shows a second modified example of the spectroscopic sensor.

FIG. 9 shows a second modified example of the spectroscopic sensor in which multilayer thin films in parallel to the semiconductor substrate 10 are formed without using the tilted structure 50. The spectroscopic sensor shown in FIG. 9 includes a semiconductor substrate 10, photodiodes 31, 32, angle limiting filters 41, 42, light band-pass filters 61, 62, and an insulating layer 70.

In the second modified example, the parts to the angle limiting filters 41, 42 are formed by the semiconductor process in the same manner as those of the above described configuration examples, and the insulating layer 70 is stacked on the angle limiting filters 41, 42. Then, the multilayer thin films of the light band-pass filters 61, 62 are formed on the insulating layer 70. The multilayer thin films have different film thicknesses in response to the transmission wavelengths of the light band-pass filters 61, 62, and are stacked at separate forming steps. That is, when one of the light band-pass filters 61, 62 is formed, the multilayer thin films are stacked while the other is covered by a photo resist or the like, and thereby, the multilayer thin films having different film thicknesses are formed.

Figure 10:
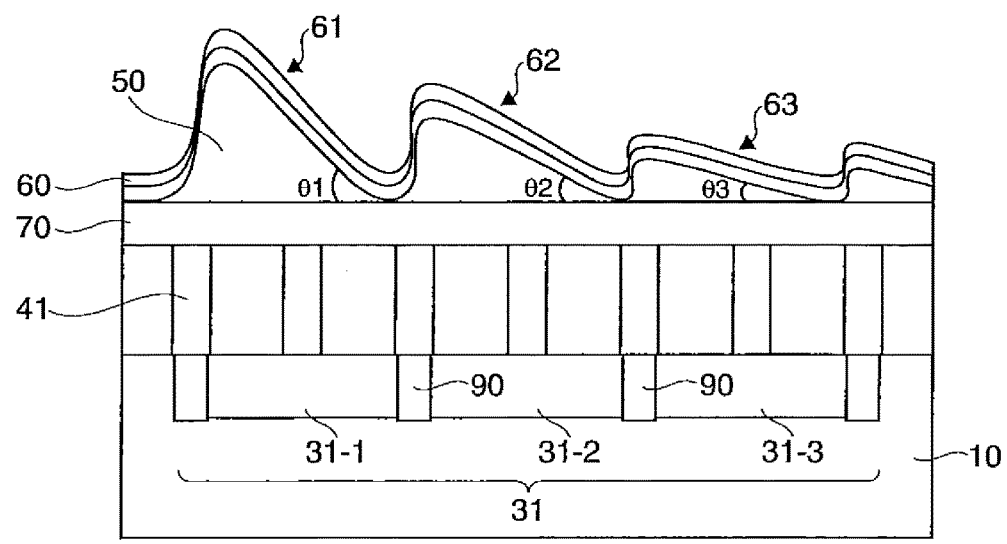
FIG. 10 shows a third modified example of the spectroscopic sensor.

FIG. 10 shows a third modified example of the spectroscopic sensor in which impurity regions for photodiodes are sectioned by trenches. The spectroscopic sensor shown in FIG. 10 includes a semiconductor substrate 10, photodiodes 31, 32, angle limiting filters 41, 42, a tilted structure 50, light band-pass filters 61 to 63, and an insulating layer 70. The photodiode 32 is the same as the photodiode 31, and its illustration and explanation will be omitted.

In the third modified example, the impurity region of the photodiode 31 is sectioned by trenches 90, and photodiodes 31-1 to 31-3 are formed. The trenches 90 are formed by an insulator trench structure of STI (Shallow Trench Isolation) or the like, for example. On the tilted structure 50, tilted surfaces at tilt angles θ1 to θ3 are formed, and the respective tilted surfaces correspond to the photodiodes 31-1 to 31-3, respectively. Then, the light band-pass filters 61 to 63 having different tilt angles are formed on the respective photodiodes 31-1 to 31-3, respectively.

In FIG. 10, one light band-pass filter is provided on one photodiode (one region) sectioned by the trench structure, however, in the embodiment, one light band-pass filter may be provided on plural photodiodes (plural regions) sectioned by the trench structure.

Figure 11:
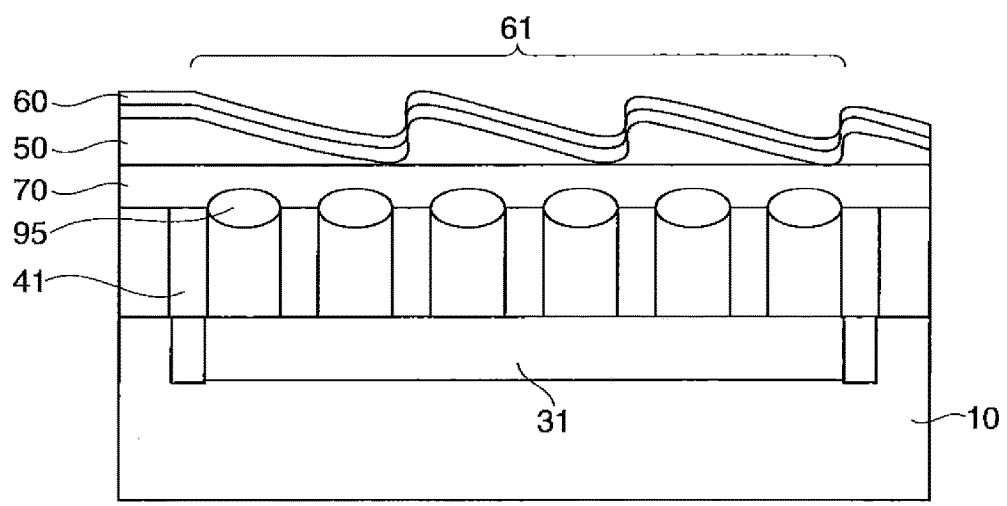
FIG. 11 shows a fourth modified example of the spectroscopic sensor.

FIG. 11 shows a fourth modified example of the spectroscopic sensor in which amounts of incident lights are increased using a micro-lens array (MLA). The spectroscopic sensor shown in FIG. 11 includes a semiconductor substrate 10, photodiodes 31, 32, angle limiting filters 41, 42, a tilted structure 50, light band-pass filters 61, 62, an insulating layer 70, and a micro-lens array 95. The photodiode 32 is the same as the photodiode 31, and its illustration and explanation will be omitted.

In the fourth modified example, micro-lenses are formed in the respective openings of the angle limiting filter 41, and the micro-lens array 95 is formed by the plural micro-lenses. The micro-lens array 95 is formed by forming a pattern using photolithography after formation of the angle limiting filter 41, etching an $SiO_2$ film, and depositing a material with a higher refractive index than that of $SiO_2$, for example.

5. Transmission Wavelength Band of Light Band-Pass Filter

As described above, the transmission wavelength band of the light band-pass filter is set by the tilt angle of the multilayer thin film and the limited angle of the angle limiting filter. This point will specifically be explained using FIGS. 12A and 12B. Note that, for simplicity of explanation, the case where the film thicknesses of the light band-pass filters 61, 62 are the same will be explained as an example as below, however, in the embodiment, the film thicknesses of the light band-pass filters 61, 62 may be different in response to the tilt angles θ1, θ2. For example, in deposition of thin films, in the case where the thin films are grown in the perpendicular direction relative to the semiconductor substrate, the film thicknesses of the light band-pass filters 61, 62 may be proportional to cos θ1, cos θ2.

Figure 12A:
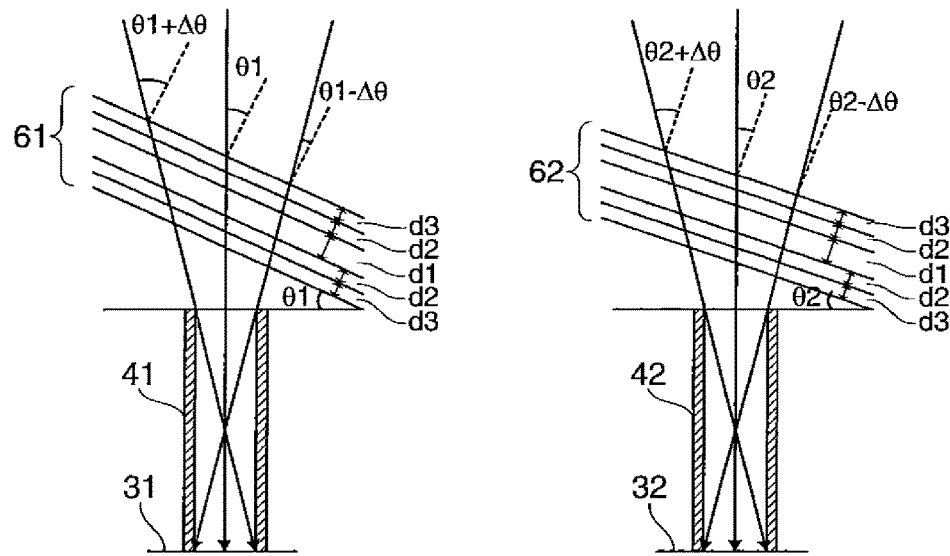
FIGS. 12A and 12B are explanatory diagrams of transmission wavelength bands of light band-pass filters.

As shown in FIG. 12A, the light band-pass filters 61, 62 are formed by thin films having thicknesses d1 to d3 (d2<d1, d3<d1). On and under the thin film having the film thickness d1, plural thin films having thicknesses d2, d3 are alternately stacked. The thin film having the film thickness d2 is formed using a material having different refractive index from those of the thin films having thicknesses d1, d3. Note that, in FIG. 12A, for simplicity, the number of layers of the thin films having thicknesses d2, d3 is omitted, however, in practice, several tens to several hundreds of layers of the thin films are stacked on and under the thin film having the film thickness d1. Further, in FIG. 12A, one layer of the thin film having the film thickness d1 is shown for simplicity, however, in practice, plural layers are often formed.

Since the light band-pass filter 61 has a tilt angle θ1 relative to the light receiving surface of the photodiode 31, the beam perpendicular to the light receiving surface enters the light band-pass filter 61 at the angle of θ1. Further, given that the limited angle of the angle limiting filter 41 is Δθ, beams entering the light band-pass filter 61 at (θ1−Δθ) to (θ1+Δθ) reach the light receiving surface of the photodiode 31. Similarly, beams entering the light band-pass filter 62 at (θ2−Δθ) to (θ2+Δθ) reach the light receiving surface of the photodiode 32.

Figure 12B:
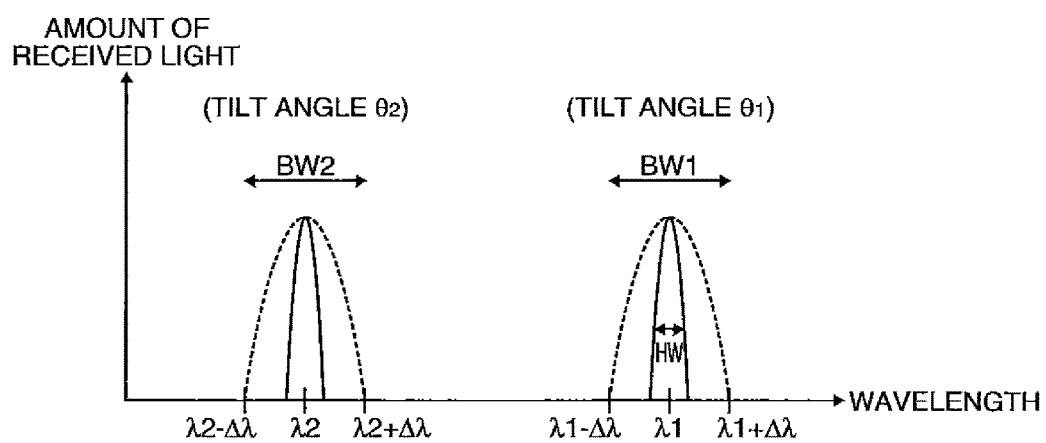

As shown in FIG. 12B, the transmission wavelength band BW1 of the light band-pass filter 61 is (λ1−Δλ) to (λ1+Δλ). In this regard, the transmission wavelength λ1=(2×n×d1×cos θ1) for the beam at the incident angle θ1. Here, n is a refractive index of the thin film having the thickness of d1. Further, (λ1−Δλ)=(2×n×d1×cos(θ1+Δθ)) and (λ1+Δλ)=(2×n×d1×cos (θ1−Δθ)). The half-value width HW (for example, HW<BW1) of the transmission wavelength for the beam at the incident angle θ1 is determined by the number of stacked layers of the multilayer films. The amount of received light of the photodiode 31 is the maximum at the incident angle θ1 perpendicular to the light receiving surface and becomes zero at the limited angle, and thus, the amount of received light of the incident light as a whole is represented by a curve shown by a dotted line. The transmission wavelength band BW2 of the light band-pass filter 62 is similarly (λ2−Δλ) to (λ2+Δλ). For example, in the case where θ2<θ1, λ2=(2×n×d1×cos θ2)<λ1=(2×n×d1×cos θ1).

According to the embodiment, the angle limiting filters 41, 42 limit the incident angles of the incident lights to (θ1−Δθ) to (θ1+Δθ), (θ2−Δθ) to (θ2+Δθ) and limit the change ranges of the transmission wavelengths to (λ1−Δλ) to (λ1+Δλ), (λ2−Δλ) to (λ2+Δλ). For the light band-pass filters, the bands BW1, BW2 of the specific wavelengths to be transmitted are set according to the change ranges of the transmission wavelengths limited to (λ1−Δλ) to (λ1+Δλ), (λ2−Δλ) to (λ2+Δλ) by the angle limiting filters 41, 42.

In this manner, the transmission wavelength bands BW1, BW2 of the light band-pass filters may be limited by the angle limiting filters 41, 42, and only the lights in the wavelength bands to be measured may be sensed. For example, the limited angles of the angle limiting filters 41, 42 are set to Δθ≤30°. Desirably, the limited angles of the angle limiting filters 41, 42 are set to Δθ≤20°.

As above, as shown in FIGS. 1A and 1B, the case where the light blocking member 120 is provided between the light source unit 110 and the spectroscopic sensor 100 and the light entering from the light source unit 110 to the spectroscopic sensor 100 not via the object of observation is blocked has been described. However, in the case where the object of observation is dynamic, a gap may be produced between the object of observation and the light blocking member 120 and a slight amount of the light from the light source unit 110 not via the object of observation may enter the spectroscopic sensor 100. In this case, the incident angle of the light not via the object of observation becomes a deeper angle (for example, incident angle >30°).

As described above, since the angle limiting filters 41, 42 limit the incident angle of the spectroscopic filter 100 to from 20° to 30°, in the case where the object of observation is dynamic, the lights entering the spectroscopic sensor 100 from the light source unit 110 not via the object of observation may be eliminated. Further, there is the same effect not only for the lights from the light source unit 110, but other lights (for example, outside lights such as sunlight and fluorescent lights) entering from the gap produced between the object of observation and the light blocking member 120 in the case where the object of observation is dynamic. The angle limiting filters 41, 42 also have the additional effects.

6. First Manufacturing Method of Spectroscopic Sensor

An example of a manufacturing method of the spectroscopic sensor in the first detailed configuration example will be explained using FIGS. 13 to 15.

Figure 13:
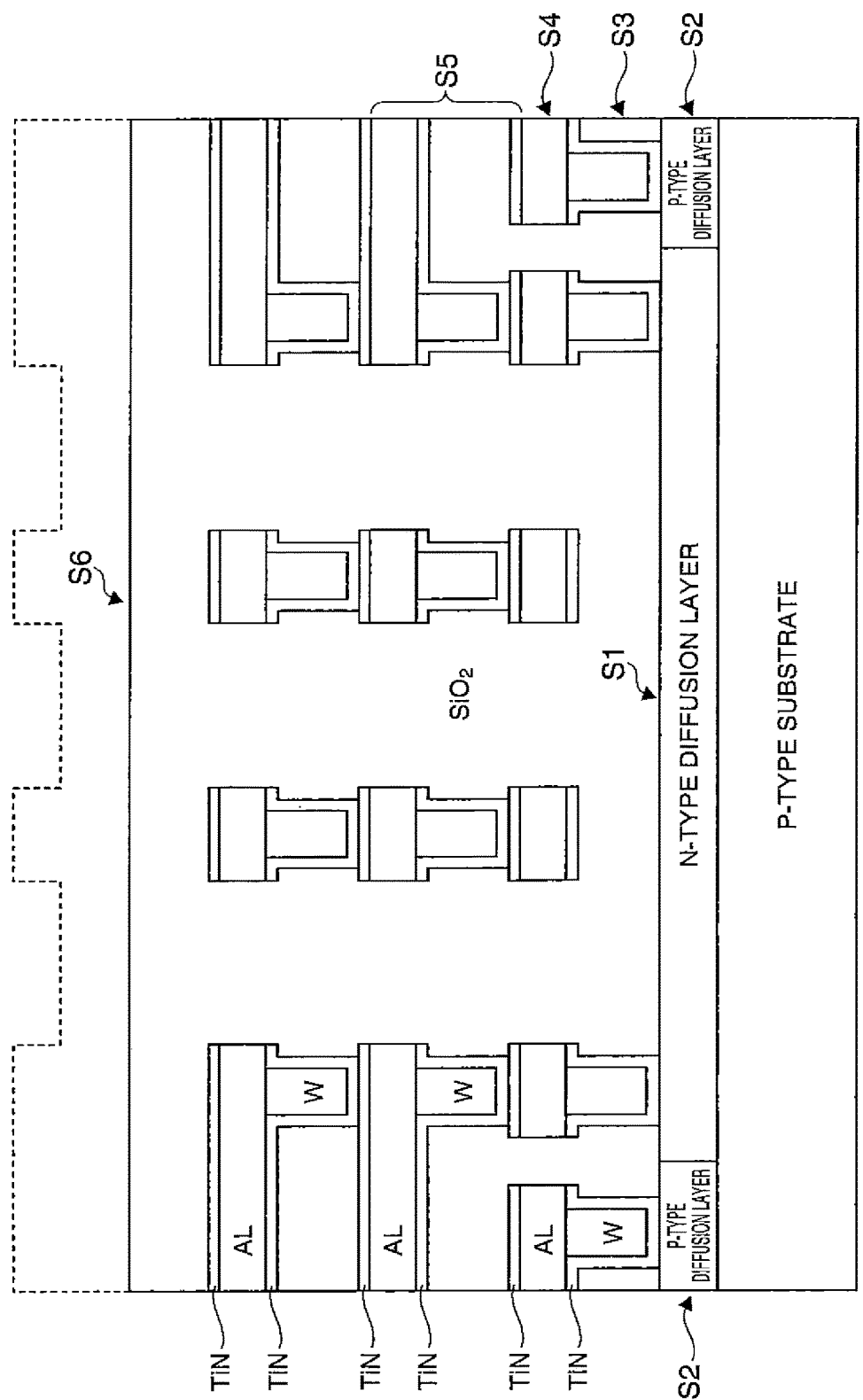
FIG. 13 shows a first manufacturing method of the spectroscopic sensor.

First, as shown by S1 in FIG. 13, a N-type diffusion layer (an impurity region of a photodiode) is formed on a P-type substrate at steps of photolithography, ion implantation, and photoresist stripping. As shown by S2, a P-type diffusion layer is formed on the P-type substrate at steps of photolithography, ion implantation, photoresist stripping and heat treatment. The N-type diffusion layer serves as a cathode of the photodiode, and the P-type diffusion layer (P-type substrate) serves as an anode.

Then, as shown by S3, contacts are formed. In the forming steps, first, at steps of deposition of $SiO_2$, and planarization by CMP, an insulating film is formed. Then, at steps of photolithography, anisotropic dry etching of $SiO_2$, and photoresist stripping, contact holes are formed. Then, at steps of sputtering of TiN, deposition of W (tungsten), and etching back of W, embedding of contact holes is performed. Then, as shown by S4, at steps of sputtering of AL (aluminum), sputtering of TiN, photolithography, anisotropic dry etching of AL and TiN, and photoresist stripping, a first AL wiring is formed.

As shown by S5, at the same steps as S3, S4, via contacts and a second AL wiring are formed. Then, the step of S5 is repeated at a necessary number of times. FIG. 13 shows the case where the third AL wiring has been formed. Then, as shown by S6, at steps of deposition of $SiO_2$ (shown by a dotted line), and planarization by CMP, an insulating film is formed. In the wiring forming steps thus far, the AL wirings and the tungsten plugs forming the angle limiting filters are stacked.

Figure 14:
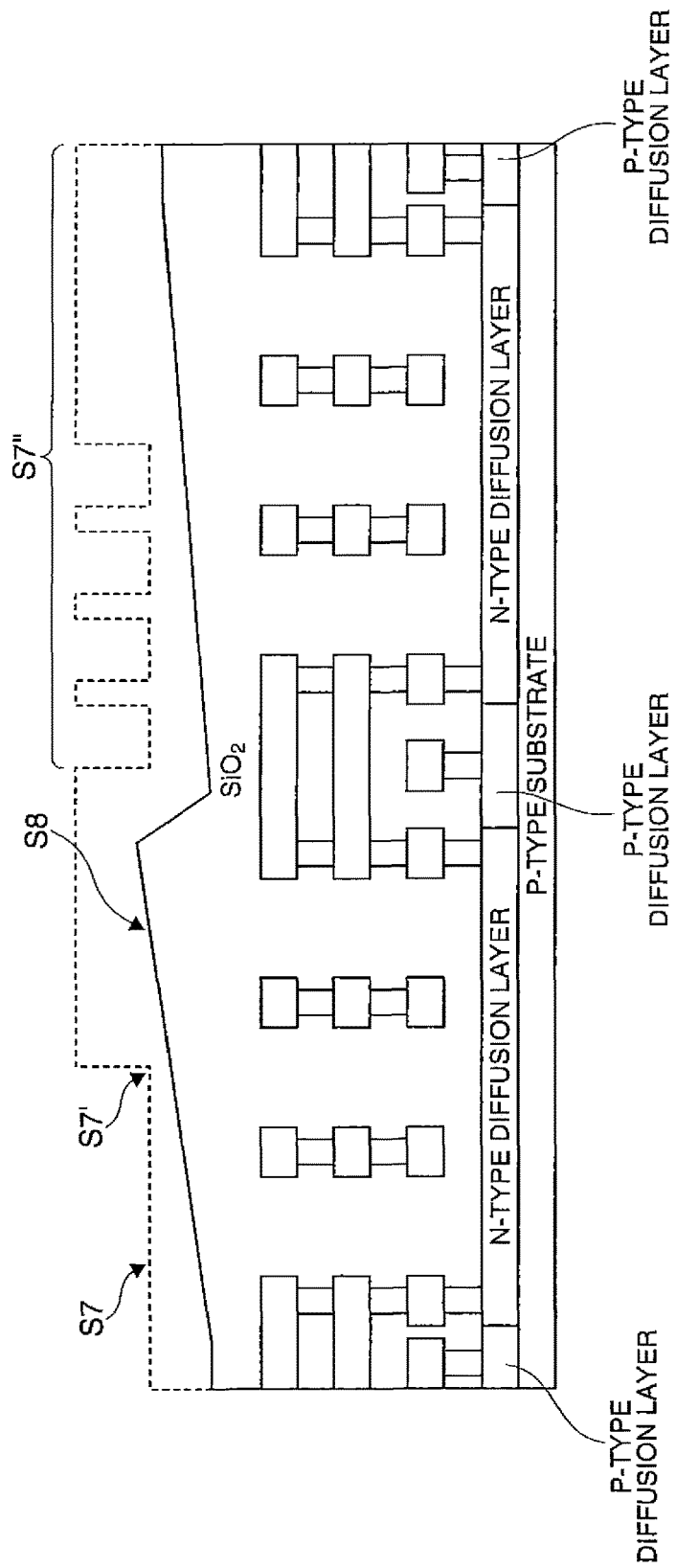
FIG. 14 shows the first manufacturing method of the spectroscopic sensor.

Then, as shown by S7 in FIG. 14, at steps of deposition of $SiO_2$, photolithography, anisotropic dry etching of $SiO_2$, and photoresist stripping, the steps S7' or the sparse and dense pattern S7" of the insulating film (shown by a dotted line) is formed.

Then, as shown by S8, at the step of grinding by CMP, tilted surfaces of the tiled structure are formed. The tilted surfaces of the tiled structure are processed at tilt angles in response to the steps or the sparse and dense pattern of the insulating film.

Figure 15:
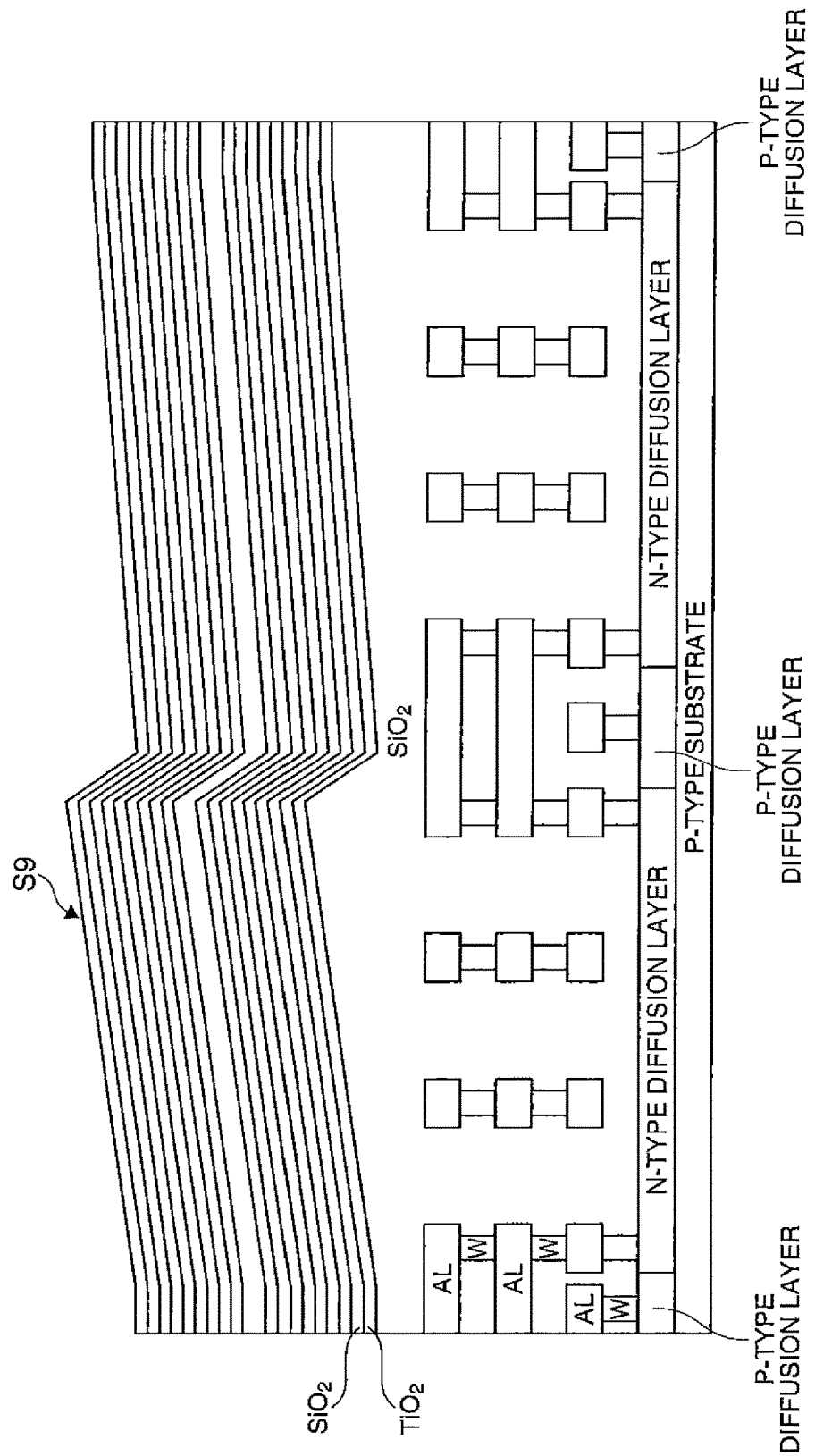
FIG. 15 shows the first manufacturing method of the spectroscopic sensor.

Then, as shown by S9 in FIG. 15, a multilayer thin film is formed on the tilted surface by alternately performing sputtering of $TiO_2$ (titanium oxide film) and sputtering of $SiO_2$. The $TiO_2$ film is a thin film with a high refractive index, and the $SiO_2$ film is a thin film with a lower refractive index than that of the $TiO_2$ film.

7. Second Detailed Configuration Example of Spectroscopic Sensor

In the above described embodiment, the case where the angle limiting filters are formed by wiring layers has been explained, however, in the embodiment, angle limiting filters may be formed on the rear surface of the semiconductor substrate using silicon trenches.

A second detailed configuration example of the spectroscopic sensor will be explained using FIGS. 16A to 17. As below, the configuration of the spectroscopic sensor of the embodiment will be schematically shown for simplicity, and the dimensions and ratios in the drawings are different from those of the real one.

Figure 16A:
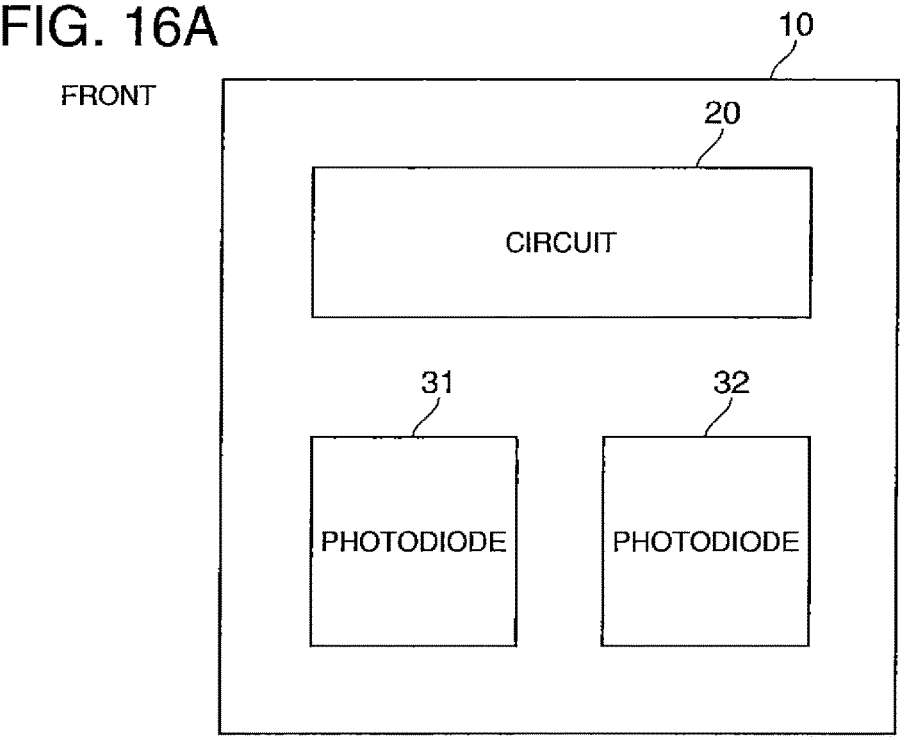
FIGS. 16A and 16B show a second detailed configuration example of the spectroscopic sensor.
Figure 16B:
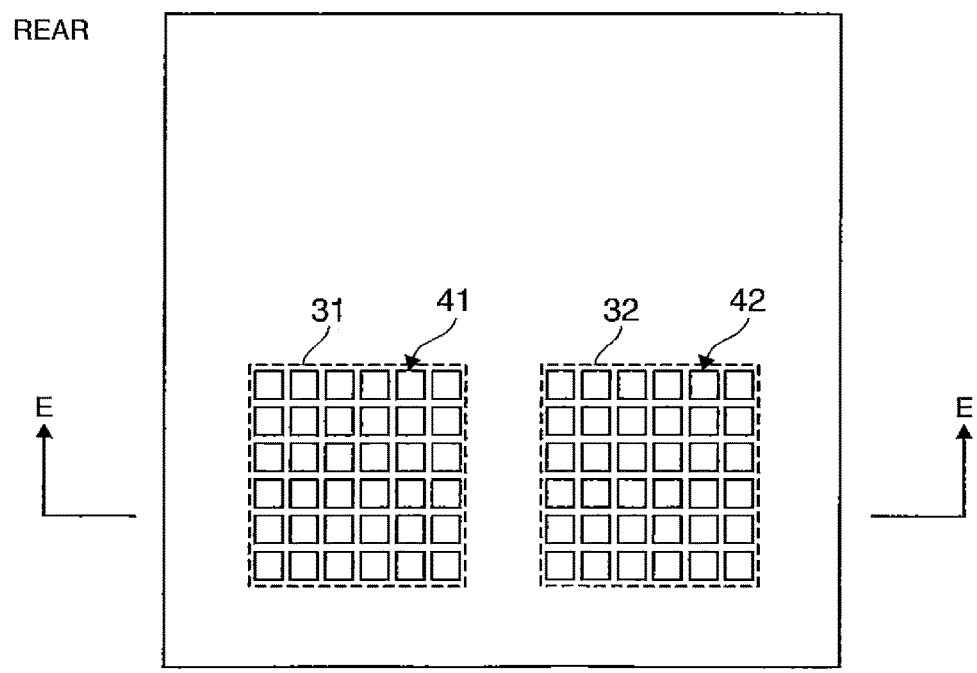

FIGS. 16A and 16B show plan views with respect to a semiconductor substrate 10 on which the spectroscopic sensor is formed. The spectroscopic sensor shown in FIGS. 16A and 16B includes a semiconductor substrate 10, a circuit 20, first and second photodiodes 31, 32, and first and second angle limiting filters 41, 42. As will be described later, the multilayer filters are formed on the first and second angle limiting filters 41, 42, however, their illustration is omitted for simplicity in FIGS. 16A and 16B.

FIG. 16A is the plan view seen from the front side on which impurity regions, wiring layers, etc. are formed in the plan view seen from a direction perpendicular to the plane of the semiconductor substrate 10. On the front side of the semiconductor substrate 10, the photodiodes 31, 32 and the circuit 20 are formed using a semiconductor process.

FIG. 16E is the plan view seen from the rear side in the plan view seen from a direction perpendicular to the plane of the semiconductor substrate 10. On the rear side of the semiconductor substrate 10, the angle limiting filters 41, 42 are formed using silicon trenches toward the photodiodes 31, 32 formed on the front side. The angle limiting filters 41, 42 are formed in lattice forms in the plan view, for example, and limit the incident angles of incident lights entering the photodiodes 31, 32 from the rear side of the semiconductor substrate 10.

Here, the silicon trench is a technique of trenching the semiconductor substrate 10 using a semiconductor process or MEMS (Micro-Electro-Mechanical System). For example, it is a technique of forming holes, grooves, steps, or the like by dry etching on a silicon substrate.

Note that the configuration of the spectroscopic sensor of the embodiment is not limited to the configuration in FIGS. 16A, 16B, but various changes may be made by omitting part of its component elements (e.g., the circuit 20), or adding other component elements.

Figure 17:
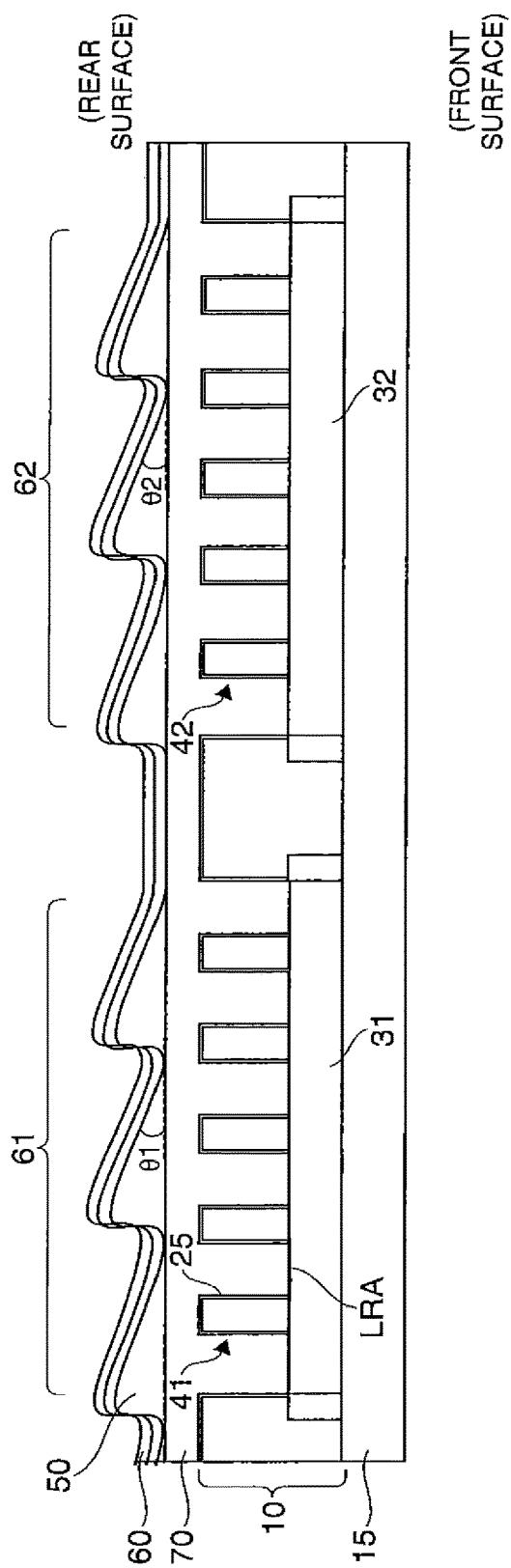
FIG. 17 shows the second detailed configuration example of the spectroscopic sensor.

FIG. 17 shows a sectional view of the spectroscopic sensor along E-E section shown in FIG. 16B. The spectroscopic sensor shown in FIG. 17 includes a semiconductor substrate 10, a wiring layer 15, light blocking materials 25, photodiodes 31, 32, angle limiting filters 41, 42, a tilted structure 50, first light band-pass filters 61, 62, and an insulating layer (a transparent film in a broad sense).

Here, "on" in the embodiment refers to a direction perpendicular to the plane of the semiconductor substrate 10 and away from the semiconductor substrate 10. That is, on the rear side, the direction away from the semiconductor substrate 10 is referred to as "on".

As shown in FIG. 17, the photodiodes 31, 32 are formed on the front side of the semiconductor substrate 10. The photodiodes 31, 32 are formed by forming P-type and N-type impurity regions using ion implantation or the like, and realized by P-N junction between the impurity regions.

On the photodiodes 31, 32, the wiring layer 15 is formed. The wiring layer 15 is stacked at forming steps of the above described circuit 20 etc. The output signals from the photodiodes 31, 32 are input to the above described circuit etc. by the wirings within the wiring layer 15, and detection-processed.

On the rear side of the semiconductor substrate 10, the angle limiting filters 41, 42 are formed. The angle limiting filters 41, 42 are formed by the semiconductor substrate 10 left after silicon trenching. On side surfaces (wall surfaces) of holes trenched by silicon trenching and the rear surface of the semiconductor substrate 10, a light blocking material (a light absorbing material or a light reflecting material) is provided (formed, stacked). On the other hand, on the bottom surfaces of the holes as light receiving surfaces of the photodiodes, no light blocking material is provided. Further, the wall surfaces of the holes trenched by silicon trenching become wall surfaces of the angle limiting filters 41, 42, and block light so that incident lights at limited angles or more may not enter the photodiodes 31, 32. The aspect ratios of the angle limiting filters 41, 42 are set in response to the transmission wavelength bands (e.g., BW1, BW2, which have been described later in FIG. 12B).

On the angle limiting filters 41, 42, the insulating film 70 filling the opening parts (hollow parts) of the angle limiting filters 41, 42 is formed. For example, the insulating film 70 is formed by an insulating film of $SiO_2$ (silicon oxide film) or the like. Note that the insulating film 70 does not necessarily have an insulation property as long as it may be a transparent material with respect to the wavelengths detected by the photodiodes 31, 32.

On the insulating film 70, the tilted structure 50 is formed. The tilted structure 50 has tilted surfaces at tilt angles $\theta 1$, $\theta 2$ in response to the transmission wavelengths of the light band-pass filters 61, 62. On the tilted structure 50, the multilayer thin film 60 forming the light band-pass filters 61, 62 is stacked. The transmission wavelength bands of the light band-pass filters 61, 62 are determined by the tilt angles $\theta 1$, $\theta 2$ of the tilted structure 50 and limited angles of the angle limiting filters 41, 42.

Note that the above described first to fourth modified examples may be applied to the second detailed configuration example. That is, the tilted structure 50 may be formed using low-melting-point glass or the like and bonded onto the angle limiting filters 41, 42. Further, multilayer thin films in parallel to the semiconductor substrate 10 may be formed with respect to each transmission wavelength. Furthermore, the photodiodes 31, 32 may be sectioned into plural photodiodes by STI. In addition, MLA for increasing the amounts of light may be provided in the openings of the angle limiting filters 41, 42.

According to the second detailed configuration example, the angle limiting filters 41, 42 are formed by forming holes for receiving lights in which light blocking materials (light absorbing films or light reflecting films or light absorbing films+light reflecting films) are provided on the rear side surfaces and wall surfaces towards the impurity regions for the photodiodes 31, 32 from the rear side of the semiconductor substrate 10.

Thereby, the spectroscopic sensor may be formed using the semiconductor process or the MEMS technology, and downsizing of the spectroscopic sensor or the like may be realized. That is, the photodiodes 31, 32 are formed by the semiconductor process and the angle limiting filters 41, 42 are formed by rear side trenching of the semiconductor substrate 10, and thus, microfabrication may easily be performed and downsizing may be realized.

Further, in the embodiment, the angle limiting filters 41, 42 are formed along the outer circumferences of the light receiving areas (for example, the areas LRA shown in FIG. 17) of the photodiodes 31, 32 in the plan view with respect to the semiconductor substrate 10. Specifically, plural light receiving areas are set in the impurity regions for the photodiodes 31, 32, and plural openings are formed along the outer circumferences of the plural light receiving areas. For example, as shown in FIGS. 16A and 16B, square light blocking materials surround the respective light receiving areas in the plan view, and the squares are arranged in the lattice forms to form the angle limiting filters 41, 42.

In this manner, the angle limiting filters 41, 42 are formed along the outer circumferences of the respective light receiving areas of photodiodes 31, 32, and thus, the incident angles of the incident lights to the respective light receiving areas of the photodiodes 31, 32 may be limited.

8. Second Manufacturing Method of Spectroscopic Sensor

An example of a manufacturing method of the spectroscopic sensor in the second detailed configuration example will be explained using FIGS. 18 to 20.

Figure 18:
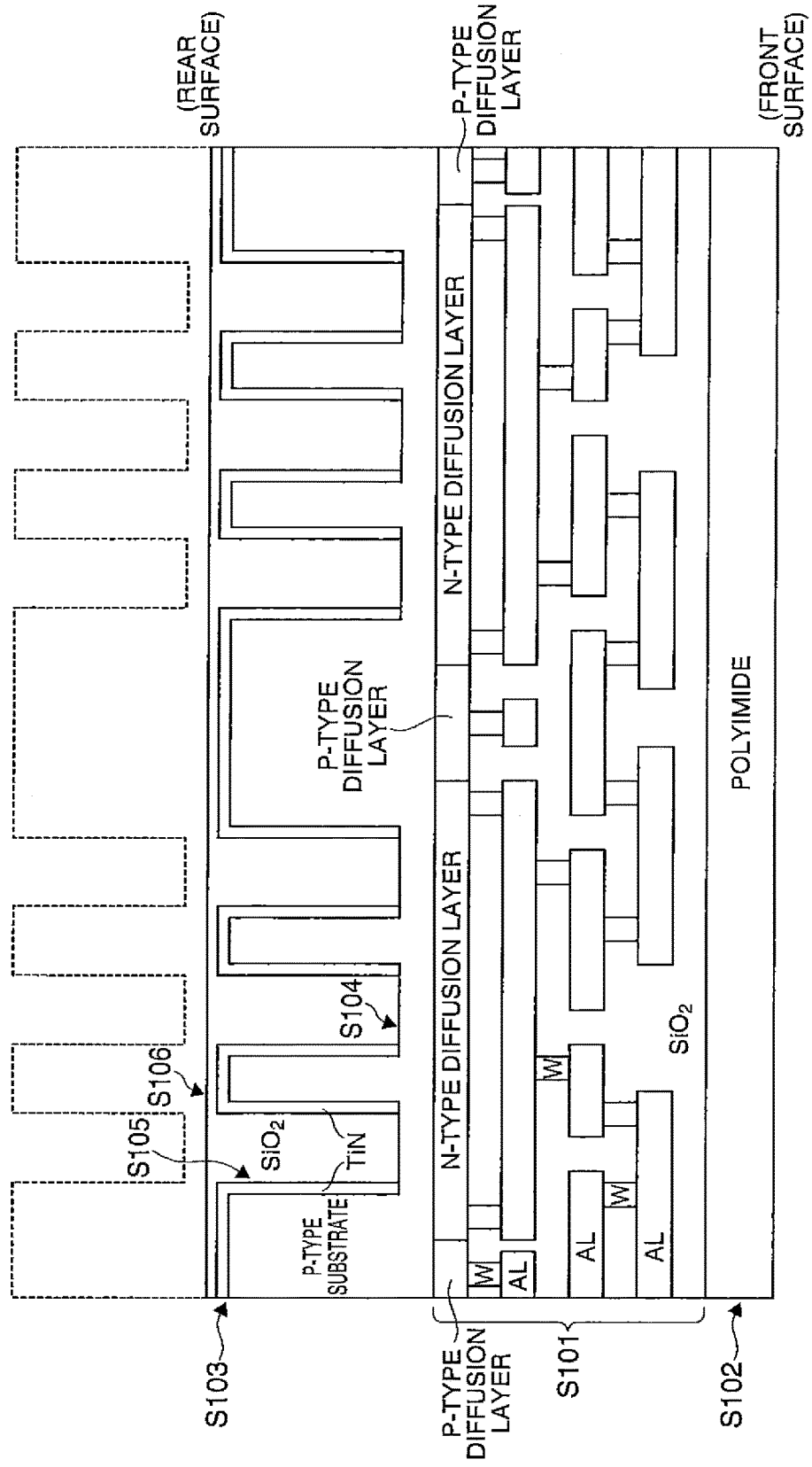
FIG. 18 shows a second manufacturing method of the spectroscopic sensor.

First, as shown by S101 in FIG. 18, at the steps described above by S1 to S6 in FIG. 13, photodiodes and a wiring layer are formed on the front side of the substrate. Then, as shown by S102, a passivation film is formed on the insulating film at steps of polyimide coating, and curing.

Then, as shown by S103, the thickness of the P-type silicon substrate is adjusted by grinding the rear surface of the P-type silicon substrate. Then, as shown by S104, at steps of photolithography, anisotropic dry etching of the P-type silicon substrate, and photoresist stripping, silicon trenches are formed.

Then, as shown by S105, at steps of deposition of TiN films, and anisotropic dry etching of the TiN films, light absorbing films (anti-reflection films) of TiN are formed on the side surfaces (inner walls) of the silicon trenches and the rear surface of the semiconductor substrate. Then, as shown by S106, at steps of deposition of a $SiO_2$ film (shown by a dotted line), and planarization of the $SiO_2$ film by CMP, embedding of the silicon trenches are performed. In this manner, the angle limiting filters are formed at the steps of S103 to S106.

Figure 19:
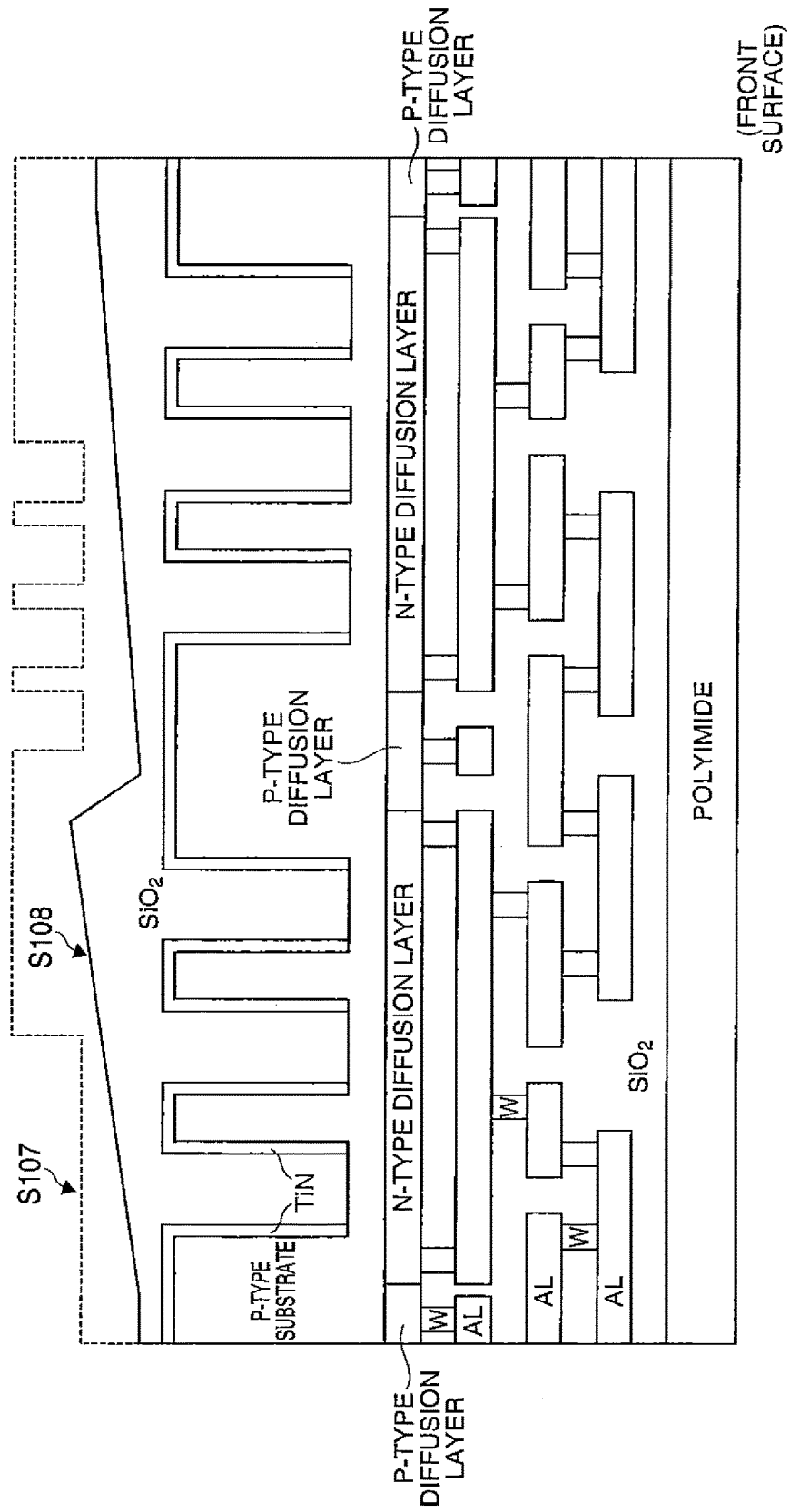
FIG. 19 shows the second manufacturing method of the spectroscopic sensor.

Then, as shown by S107 in FIG. 19, at steps of deposition of a $SiO_2$ film, photolithography, anisotropic dry etching of the $SiO_2$ film, and photoresist stripping, steps or a sparse and dense pattern of the insulating film are formed. Then, as shown by S108, at the step of grinding of the $SiO_2$ film, tilted surfaces of the tiled structure are formed. In this regard, the tilted surfaces of the tiled structure are processed at tilt angles in response to the steps or the sparse and dense pattern of the insulating film.

Figure 20:
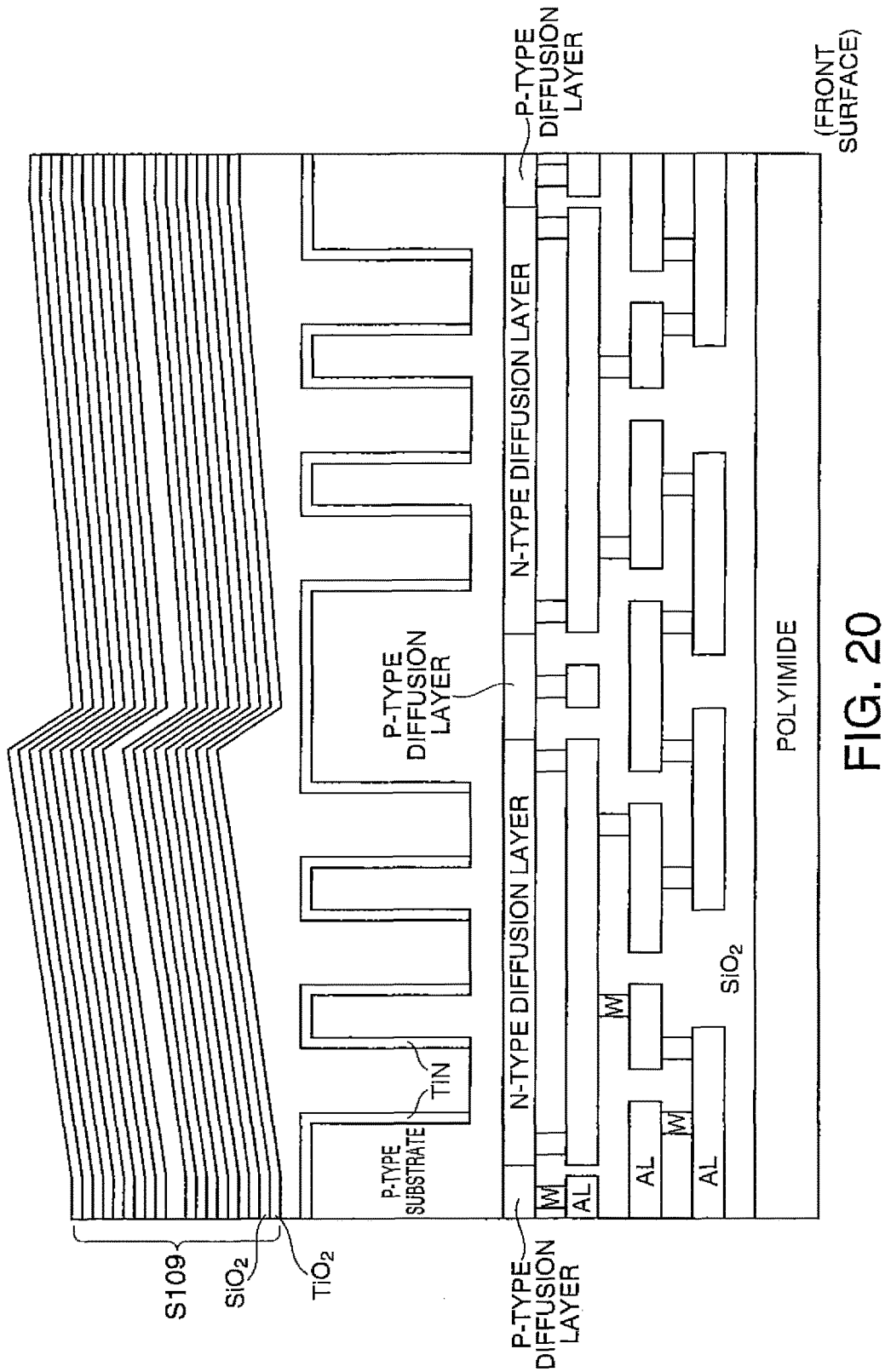
FIG. 20 shows the second manufacturing method of the spectroscopic sensor.

Then, as shown by S109 in FIG. 20, a multilayer thin film is formed on the tilted surfaces by alternately performing sputtering of $TiO_2$ (titanium oxide film) and sputtering of $SiO_2$. The $TiO_2$ film is a thin film with a high refractive index, and the $SiO_2$ film is a thin film with a lower refractive index than that of the $TiO_2$ film.

9. Electronic Equipment

Figure 21:
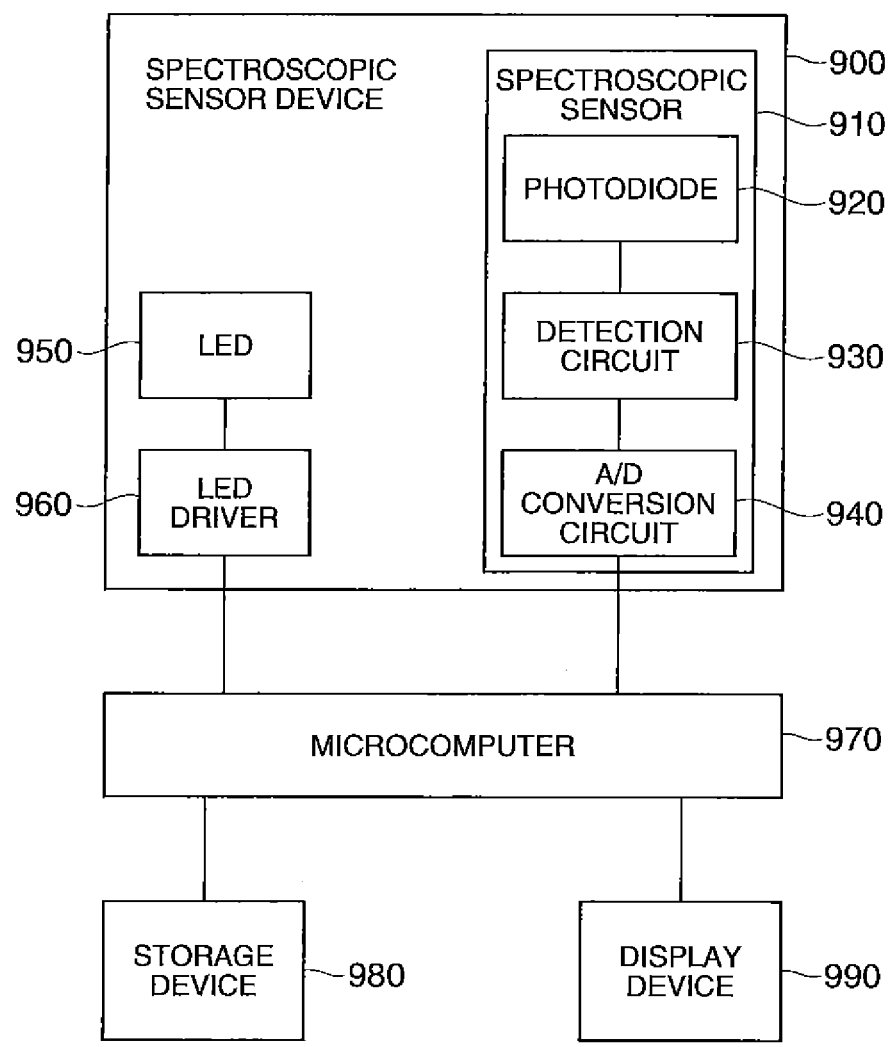
FIG. 21 shows a configuration example of electronic equipment.

FIG. 21 shows a configuration example of electronic equipment including the spectroscopic sensor device of the embodiment. For example, as electronic equipment, a pulsimeter, a pulse oximeter, a blood sugar meter, a fruit sugar content meter, or the like is assumed.

The electronic equipment shown in FIG. 21 includes a spectroscopic sensor device 900, a microcomputer 970 (CPU), a storage device 980, and a display device 990. The spectroscopic sensor device 900 includes an LED 950 (light source), an LED driver 960, and a spectroscopic sensor 910. The spectroscopic sensor 910 is integrated in one chip of IC, for example, and includes a photodiode 920, a detection circuit 930, and an A/D conversion circuit 940.

The LED 950 applies white light, for example, to an object of observation. The spectroscopic sensor device 900 spectroscopically separates the reflected light and the transmitted light from the object of observation, and acquires signals of the respective wavelengths. The microcomputer 970 controls the LED driver 960 and acquires signals from the spectroscopic sensor 910. The microcomputer 970 displays representation based on the acquired signals on the display device 990 (for example, a liquid crystal display device) or stores data based on the acquired signals in the storage device 980 (for example, a memory or a magnetic disc).

The embodiment has been specifically explained as described above, however, a person skilled in the art may easily understand that many modifications without substantially departing from new matter and effects of the invention may be made. Therefore, the modified examples are within the scope of the invention. For example, in specifications or drawings, terms (photosensor, thin-film filter, semiconductor substrate, etc.) described with terms (photodiode, light bandpass filter, silicon substrate, etc.) in broader senses or synonyms at least at once may be replaced by the different terms in any part of the specifications or drawings. Further, the configurations and operations of the spectroscopic sensor, the spectroscopic sensor device, electronic equipment, etc. are not limited to those that have been explained in the embodiment, but various changes may be embodied.

What is claimed is:
1. A pulsimeter comprising:
a light source unit that transmits light to a body of a user; and
a spectroscopic sensor that receives incident light from the light source unit reflected from or transmitted through the body of the user,
the spectroscopic sensor including:
a photosensor that has an impurity area formed on a semiconductor substrate, and
an angle limiting filter that includes a plurality of light blocking materials which have electrical conductivity, at least one of the light blocking materials being disposed directly on and contacting the impurity area.
2. The pulsimeter of claim 1, wherein
the light blocking material includes a light absorbing material.
3. The pulsimeter of claim 1, wherein
the light blocking material is formed by a conducting plug provided in an insulating material disposed on the semiconductor substrate.
4. The pulsimeter of claim 3, wherein
the conducting plug is formed in a contact hole provided in the insulating material.
5. The pulsimeter of claim 1, wherein
the light blocking material is comprised of tungsten or titanium nitride.
6. The pulsimeter of claim 1, wherein
the plurality of light blocking materials is formed in lattice form in a plan view.
7. The pulsimeter of claim 1, wherein
the angle limiting filter transmits an electrical signal from the impurity region.
8. The pulsimeter of claim 1, wherein
the angle limiting filter is an electrode of the spectroscopic sensor.
9. The pulsimeter of claim 1, wherein
the plurality of light blocking materials is disposed directly on and contacting the impurity area.
10. A spectroscopic sensor comprising:
a light source unit that transmits light to a body of a user; and
a photo sensor that detects incident light from the light source unit reflected from or transmitted through the body of the user,
the photo sensor comprising:
an impurity area formed on a semiconductor substrate, and
an angle limiting filter that is formed by a plurality of light blocking materials which have electrical conductivity, at least one of the light blocking materials being disposed directly on and contacting the impurity area.
11. The spectroscopic sensor of claim 10, wherein
the light blocking material includes a light absorbing material.
12. The spectroscopic sensor of claim 10, wherein
the light blocking material is formed by a conducting plug provided in an insulating material disposed on the semiconductor substrate.

13. The spectroscopic sensor of claim 12, wherein the conducting plug is formed in a contact hole provided in the insulating material.
14. The spectroscopic sensor of claim 10, wherein the light blocking material is comprised of tungsten or titanium nitride.
15. The spectroscopic sensor of claim 10, wherein the plurality of light blocking materials is formed in lattice form in a plan view.
16. The spectroscopic sensor of claim 10, wherein the angle limiting filter transmits an electrical signal from the impurity region.
17. The spectroscopic sensor of claim 10, wherein the angle limiting filter is an electrode of the photo sensor.
18. The spectroscopic sensor of claim 10, wherein the plurality of light blocking materials is disposed directly on and contacting the impurity area.

* * * * *